(12) United States Patent
Jones et al.

(10) Patent No.: US 7,723,450 B2
(45) Date of Patent: May 25, 2010

(54) TRANSITION METAL COMPOUND, LIGAND SYSTEM, CATALYST SYSTEM AND PROCESS FOR PREPARING POLYOLEFINS

(75) Inventors: Robert L. Jones, Frankfurt (DE);
Michael J. Elder, Rockville, MD (US);
Jennifer Kipke, Frankfurt (DE);
Alexander Koeppl, Limburgerhof (DE);
Markus Schopf, Bonn (DE); John Ewen, Lake Placid, FL (US)

(73) Assignee: Basell Polyolefine GmbH, Wesseling (DE)

( * ) Notice: Subject to any disclaimer, the term of this patent is extended or adjusted under 35 U.S.C. 154(b) by 723 days.

(21) Appl. No.: 11/597,346

(22) PCT Filed: Jun. 2, 2005

(86) PCT No.: PCT/EP2005/005947

§ 371 (c)(1),
(2), (4) Date: Nov. 22, 2006

(87) PCT Pub. No.: WO2005/118654

PCT Pub. Date: Dec. 15, 2005

(65) Prior Publication Data

US 2007/0260023 A1 Nov. 8, 2007

Related U.S. Application Data

(60) Provisional application No. 60/588,701, filed on Jul. 16, 2004.

(30) Foreign Application Priority Data

Jun. 4, 2004 (DE) .................. 10 2004 027 332

(51) Int. Cl.
*C08F 4/50* (2006.01)
(52) U.S. Cl. .................. 526/160
(58) Field of Classification Search .......... 526/160
See application file for complete search history.

(56) References Cited

U.S. PATENT DOCUMENTS

| | | | |
|---|---|---|---|
| 3,125,547 A | 3/1964 | Blatz | |
| 5,489,659 A * | 2/1996 | Sugano et al. | 526/127 |
| 6,350,814 B1 | 2/2002 | Bauer et al. | |
| 6,417,302 B1 | 7/2002 | Bohnen | |
| 6,437,161 B1 | 8/2002 | Mihan et al. | |
| 6,482,902 B1 | 11/2002 | Bohnen et al. | |
| 6,589,905 B1 | 7/2003 | Fischer et al. | |
| 6,756,455 B2 * | 6/2004 | Nagy et al. | 526/161 |
| 6,812,185 B2 | 11/2004 | Fischer et al. | |
| 7,053,160 B1 | 5/2006 | Bingel et al. | |
| 7,109,278 B2 * | 9/2006 | Okumura et al. | 526/170 |
| 7,452,949 B2 * | 11/2008 | Okumura et al. | 526/160 |
| 7,504,354 B2 * | 3/2009 | Elder et al. | 502/155 |
| 2009/0082533 A1 * | 3/2009 | Elder | 526/160 |

FOREIGN PATENT DOCUMENTS

| | | |
|---|---|---|
| DE | 19745047 | 4/1999 |
| EP | 100843 | 2/1984 |
| EP | 416815 | 3/1991 |
| EP | 420436 | 4/1991 |
| EP | 662989 | 7/1995 |
| EP | 728160 | 8/1996 |
| WO | 90/03414 | 4/1990 |
| WO | 91/09882 | 7/1991 |
| WO | 95/27005 | 10/1995 |
| WO | 96/00243 | 1/1996 |
| WO | 98/03559 | 1/1998 |
| WO | 98/27124 | 6/1998 |
| WO | 98/40419 | 9/1998 |
| WO | 99/06414 | 2/1999 |
| WO | 99/24446 | 5/1999 |
| WO | 99/40129 | 8/1999 |

(Continued)

OTHER PUBLICATIONS

G. Tang et al., "Self-immobilized metallocene catalysts bearing an allyl group for ethylene polymerization, X-ray crystal structure of [(CH$_2$CHCH$_2$)CH$_3$Si(C$_{13}$H$_8$)$_2$]ZrCl$_2$," *Journal of Organometallic Chemistry*, vol. 689, p. 678-684 (2004).

(Continued)

*Primary Examiner*—Ling-Siu Choi
*Assistant Examiner*—Sonya Wright
(74) *Attorney, Agent, or Firm*—William R. Reid; Jonathan L. Schuchardt

(57) ABSTRACT

The present invention relates to organometallic transition metal compounds of the formula (I)

$$Z^1A_nZ^2MX_m \qquad (I)$$

where
$Z^1$ is a coordinating group which comprises a six-π-electron central group which coordinates directly to M,
A is a divalent bridge between the groups $Z^1$ and $Z^2$,
$Z^2$ is a coordinating group having the same meaning as $Z^1$ or is a group comprising an open pentadienyl, a cyclopentadienyl-containing group or a heterocyclic, 5- or 6-membered group containing six π electrons,
n=zero or 1,
M is an element of group 3, 4, 5 or 6 of the Periodic Table of the Elements,
the radicals X are identical or different and are each an organic or inorganic radical,
m is 0, 1 or 2,
and at least one of the three molecule fragments $Z^1$, $Z^2$ and A bears a monovalent organic radical.

4 Claims, 1 Drawing Sheet

FOREIGN PATENT DOCUMENTS

| | | |
|---|---|---|
| WO | 00/05277 | 2/2000 |
| WO | 00/31090 | 6/2000 |
| WO | 01/47939 | 5/2001 |
| WO | 01/48039 | 5/2001 |
| WO | 01/44318 | 6/2001 |
| WO | 03/045964 | 5/2003 |

OTHER PUBLICATIONS

H. Alt et al.,"$C_2$-bridged metallocene dichloride complexes of the types ($C_{13}H_8$-$CH_2$CHR-$C_9H_{6-n}R'_n$)$ZrCl_2$ and ($C_{13}H_8$-$CH_2$CHR-$C_{13}H_8$)$MCl_2$ (n=0, 1; R=H, alkenyl; R'=alkenyl, benzyl; M=Zr, Hf) as self-immobilizing catalyst precursors for ethylene polymerization," *Journal of Organometallic Chemistry*, vol. 580, p. 1-16 (1999).

S. Trinkle et al., "Van-Gurp-Palmen-plot: a way to characterize polydispersity of linear polymers," *Rheol. Acta.*, vol. 40, p. 322-328 (2001).

S. Trinkle et al., "Van-Gurp-Palmen Plot II: classification of long chain branched polymers by there topology,"*Rheol. Acta*, vol. 41, p. 103-113 (2002).

J. Ewen et al., "Chiral *Ansa* Metallocenes with Cp Ring-Fused to Thiophenes and Pyrroles: Syntheses, Crystal Structures, and Isotactic Polypropylene Catalysts," *J. Am. Chem. Soc.*, vol. 123(20), p. 4763-4773 (2001).

\* cited by examiner

TRANSITION METAL COMPOUND, LIGAND SYSTEM, CATALYST SYSTEM AND PROCESS FOR PREPARING POLYOLEFINS

This application is the U.S. national phase of International Application PCT/EP2005/005947, filed Jun. 2, 2005, claiming priority to German Patent Application 102004027332.4 filed Jun. 4, 2004, and the benefit under 35 U.S.C. 119(e) of U.S. Provisional Application No. 60/588,701, filed Jul. 16, 2004; the disclosures of International Application PCT/EP2005/005947, German Patent Application 102004027332.4 and U.S. Provisional Application No. 60/588,701, each as filed, are incorporated herein by reference.

DESCRIPTION

The present invention relates to organometallic transition metal compounds of the formula (I)

$$Z^1A_nZ^2MX_m \quad (I)$$

where $Z^1$ is a coordinating group which comprises a six-π-electron central group which coordinates directly to M and which bears at least one fused-on saturated or unsaturated $C_2$-$C_{30}$ ring system containing at least one heteroatom selected from the group consisting of the elements B, Al, Ga, In, Si, Ge, Sn, O, S, Se, Te, N, P, As and Sb in the ring, where the heteroatom is bound directly to a carbon atom of the six-π-electron-containing central group and the heteroatom may also bear radicals which are not constituents of the ring, A is a divalent bridge between the groups $Z^1$ and $Z^2$, $Z^2$ is a coordinating group having the same meaning as $Z^1$ or is a group comprising an open pentadienyl, a cyclopentadienyl-containing group or a heterocyclic, 5- or 6-membered group containing six π electrons, n=zero or 1, M is an element of group 3, 4, 5 or 6 of the Periodic Table of the Elements or is an element of the lanthanides, the radicals X are identical or different and are each an organic or inorganic radical, with two radicals X also being able to be joined to one another, m is 0, 1 or 2, and at least one of the three molecule fragments $Z^1$, $Z^2$ and A bears a monovalent organic radical which contains at least one olefinic C=C double bond and has from 2 to 40 carbon atoms.

In addition, the present invention relates to ligand systems having such a substitution pattern, catalyst systems comprising at least one of the transition metal compounds of the invention, a process for preparing polyolefins by polymerization or copolymerization of at least one olefin in the presence of one of the catalyst systems of the invention and the use of the ligand systems of the invention for preparing organometallic transition metal compounds.

Research and development on the use of organometallic transition metal compounds, in particular metallocenes, as catalyst components for the polymerization and copolymerization of olefins with the objective of preparing tailored polyolefins has been pursued intensively in universities and in industry over the past 15 years.

The ethylene-based polyolefins prepared by means of metallocene catalyst systems now represent a dynamically growing market segment.

Variation of the substitution pattern on the ligand systems of metallocenes changes the steric conditions around the active site and also its electronic structure. In this way, it is possible, for example, to influence the polymerization behavior of the catalyst constituents and ultimately also the properties of the polymers, for example comonomer content, degree of branching, chain length or molar mass and consequently the macroscopic material properties of these polymers.

In the polymerization of olefins, in particular of ethylene, the catalyst system which usually comprises at least one organometallic transition metal compound and a cocatalyst component such as an aluminoxane, a strong Lewis acid or an ionic compound can also be used in supported form in order to avoid deposit formation in the reactor.

Journal of Organometallic Chemistry 580, (1999), 1 to 16, describes ethylene-bridged fluorenyl-indenyl and bisfluorenyl metallocenes having co-alkenyl radicals, which can be used as heterogeneous catalyst systems as a result of the phenomenon of self-immobilization.

WO 01/47939 describes heterocyclic metallocenes which can advantageously be used for preparing homopolymers of propene having a reduced degree of crystallinity.

Figure 1:
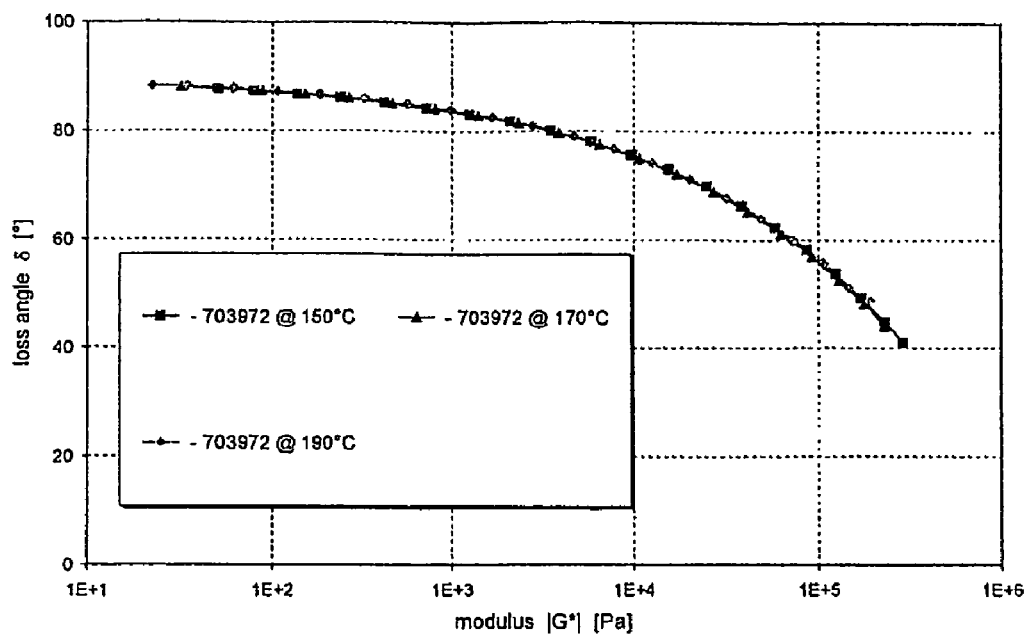
FIG. 1 illustrates a Van Gurp-Palmen plot for the polymer 703972.

It was an object of the present invention to find new organometallic transition metal compounds which can be used as catalyst constituents of catalyst systems for the polymerization of ethylene. The polyethylene prepared by means of them should have a high molar mass, a narrow molecular weight distribution and a defined chain structure depending on the molecular weight. In addition, for reasons of economics, the metallocenes to be found should be easy to synthesize and have a high activity in order to minimize catalyst costs and catalyst residues in the finished polymer.

We have accordingly found the organometallic transition metal compounds of the formula (I) mentioned at the outset.

$Z^1$ is a coordinating group, in particular a singly negatively charged group comprising a six-group π-electron central group, in particular a cyclopentadienyl group, which coordinates directly to M and bears at least one fused-on saturated or unsaturated $C_2$-$C_{30}$ ring system containing at least one heteroatom selected from the group consisting of the elements B, Al, Ga, In, Si, Ge, Sn, O, S, Se, Te, N, P, As and Sb, in particular O, S, Se, Te, N and P, preferably S and N, particularly preferably S, in the ring, where the heteroatom is bound directly to a carbon atom of the six-π-electron-containing central group and the heteroatom may also bear radicals which are not constituents of the ring. Examples of such radicals are organic radicals having from 1 to 40 carbon atoms, e.g. a cyclic, branched or unbranched $C_1$-$C_{20}$-, preferably $C_1$-$C_{10}$-alkyl radical, a $C_2$-$C_{20}$-, preferably $C_2$-$C_8$-alkenyl radical, an aryl or alkylaryl or arylalkyl radical having from 1 to 10, preferably from 1 to 4, carbon atoms in the alkyl part and from 6 to 22, preferably from 6 to 10, carbon atoms in the aryl part. Individual carbon atoms or hydrocarbon units, for example a CH or $CH_2$ group, in the radicals mentioned may also be replaced by heteroatoms such as Si, N, O or S. In determining the number of carbon atoms in the fused-on heteroatom-containing $C_2$-$C_{30}$ ring system, the ring carbons of the six-π-electron central group are not counted.

A is a divalent bridging group between the groups $Z^1$ and $Z^2$ and may comprise, in addition to the atom or the two atoms which is/are bound directly to the two groups $Z^1$ and $Z^2$, further radicals as substituents.

Examples of A are:

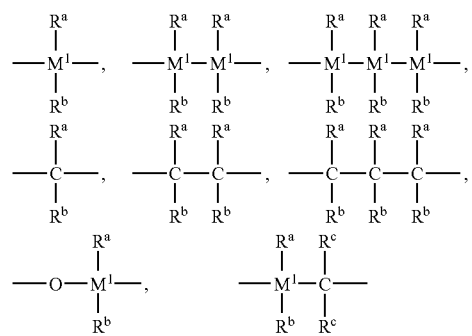

—B(R$^a$)—, —B(NR$^a$R$^b$)—, —Al(R$^a$)—, —O—, —S—, —S(O)—, —S(O$_2$)—, —N(R$^a$)—, —C(O)—, —P(R$^a$)— or —P(O)(R$^a$)—, preferably

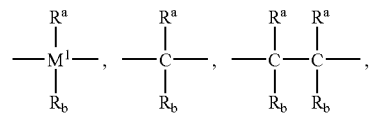

where

M$^1$ is silicon, germanium or tin, preferably silicon or germanium, particularly preferably silicon, and R$^a$, R$^b$ and R$^c$ are identical or different and are each a hydrogen atom, a halogen atom, a trimethylsilyl group, a $C_1$-$C_{10}$-, preferably $C_1$-$C_3$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-, preferably $C_1$-$C_3$-alkoxy group, a $C_7$-$C_{15}$-alkylaryloxy group, a $C_2$-$C_{10}$, preferably $C_2$-$C_4$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms.

A is preferably a substituted silylene group or a substituted ethylene group.

Z$^2$ is a coordinating group having the same meaning as Z$^1$, although Z$^2$ does not have to be identical to Z$^1$, or a group comprising an open pentadienyl, a cyclopentadienyl-containing group such as a monosubstituted or polysubstituted or unsubstituted cyclopentadienyl, indenyl or fluorenyl group, or a heterocyclic, 5- or 6-membered, six-π-electron-containing group such as a substituted or unsubstituted pyrrolyl, diborolenyl or borinate group.

n is zero or 1. When n is zero, the organometallic transition metal compound is unbridged. When n is 1, the organometallic transition metal compound is bridged. Preference is given to n being 1.

M is an element of group 3, 4, 5 or 6 of the Periodic Table of the Elements or an element of the lanthanides, for example titanium, zirconium, hafnium, vanadium, niobium, tantalum, chromium, molybdenum or tungsten, preferably titanium, zirconium, hafnium, particularly preferably zirconium and hafnium, and especially preferably zirconium.

The radicals X are identical or different, preferably identical, and are each an organic or inorganic radical, with two radicals X also being able to be joined to one another. In particular, X is halogen, for example fluorine, chlorine, bromine, iodine, preferably chlorine, hydrogen, $C_1$-$C_{20}$-, preferably $C_1$-$C_4$-alkyl, $C_2$-$C_{20}$-, preferably $C_2$-$C_4$-alkenyl, $C_6$-$C_{22}$-, preferably $C_6$-$C_{10}$-aryl, an alkylaryl or arylalkyl group having from 1 to 10, preferably from 1 to 4, carbon atoms in the alkyl part and from 6 to 22, preferably from 6 to 10, carbon atoms in the aryl part, —OR$^d$ or —NR$^d$R$^e$, preferably —OR$^d$, with two radicals X also being able to be joined to one another, preferably two radicals —OR$^d$ which are each, in particular, a substituted or unsubstituted 1,1'-bi-2-phenoxide radical. Two radicals X can also form a substituted or unsubstituted diene ligand, in particular a 1,3-diene ligand. The radicals R$^d$ and R$^e$ are each $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl part and from 6 to 22, preferably from 6 to 10, carbon atoms in the aryl part. Very particular preference is given to X being chlorine or methyl.

The index m is 0, 1 or 2, with m+2 usually corresponding to the oxidation number of M, and m is usually preferably 2 in the case of the elements of group 4 of the Periodic Table of the Elements. When M is chromium, m is preferably 0 or 1, in particular 0.

At least one of the three molecule fragments Z$^1$, Z$^2$ and A bears a monovalent organic radical which contains at least one olefinic C=C double bond and has from 2 to 40 carbon atoms. This radical can also contain heteroatoms from groups 14, 15, 16 and 17 of the Periodic Table of the Elements. Examples of such a radical are a linear or branched $C_2$-$C_{20}$-, preferably $C_2$-$C_{10}$-alkenyl radical, a $C_5$-$C_{20}$-, preferably $C_5$-$C_{10}$-cycloalkenyl radical, a $C_8$-$C_{40}$-alkenylaryl or arylalkenyl radical, where the radicals may also contain one or more heteroatoms, preferably heteroatoms selected from among the elements of the group consisting of Si, Ge, N, P, O and S, in particular Si, N and O, for example a $C_4$-$C_{20}$-alkenyldialkylsilyl radical, a $C_2$-$C_{20}$-alkenoxy radical or a $C_2$-$C_{20}$-alkenylamide radical.

Preferred examples of such radicals are allyl, 3-buten-1-yl, 5-hexen-1-yl, 7-octen-1-yl, 3-cyclohexen-1-yl, 2-(allyldimethylsilyl)ethyl, 1-(allyldimethylsiloxy)methyl, 4-(2-cyclopentenyl)but-1-yl, 4-(3-butenyldimethylsiloxy)phenyl, 5-hexenyloxy, dimethyl-7-octenylsilyl, 6-(3-butenyl)pyrid-2-yl, 3,5-hexadienyl, 4-(5-hexenyl)phenyl and 4-(7-octenyl)benzyl.

Preference is given to organometallic transition metal compounds as described above wherein the organometallic transition metal compound comprises the formula II (II)

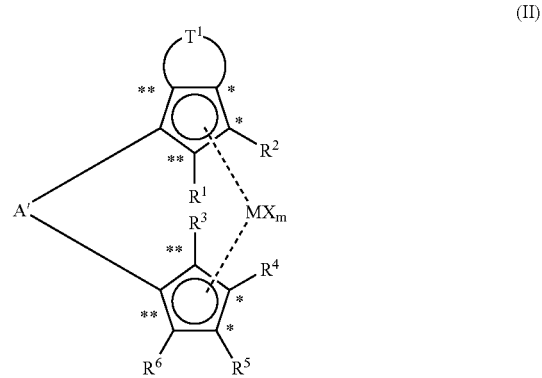

where

M is an element of group 3, 4, 5 or 6 of the Periodic Table of the Elements or an element of the lanthanides, the radicals X are identical or different and are each an organic or inorganic radical, with two radicals X also being able to be joined to one another to form a divalent radical, m is 0, 1 or 2,

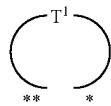

is a divalent group

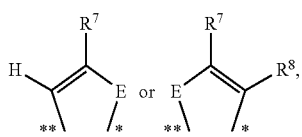

$R^1$ is hydrogen or an organic radical having from 1 to 40 carbon atoms, $R^2$ is hydrogen or an organic radical having from 1 to 40 carbon atoms, or $R^1$ and $R^2$ together form a divalent group

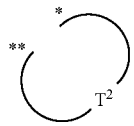

which is

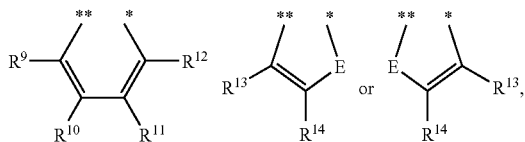

$R^3$ is hydrogen or an organic radical having from 1 to 40 carbon atoms, $R^4$ is hydrogen or an organic radical having from 1 to 40 carbon atoms, or $R^3$ and $R^4$ together form a divalent group

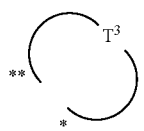

which is

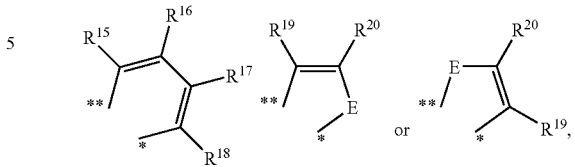

$R^5$ is hydrogen or an organic radical having from 1 to 40 carbon atoms, $R^6$ is hydrogen or an organic radical having from 1 to 40 carbon atoms, or $R^5$ and $R^6$ together form a divalent group

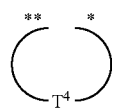

which is

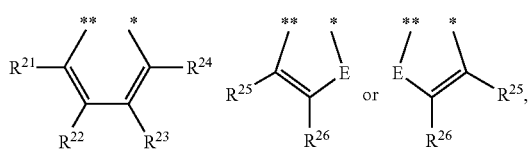

$R^7$, $R^8$ are identical or different and are each hydrogen or an organic radical having from 1 to 40 carbon atoms or $R^7$ and $R^8$ together with the atoms connecting them form a monocyclic or polycyclic ring system which may in turn be substituted, $R^9$, $R^{10}$, $R^{11}$ and $R^{12}$ are identical or different and are each hydrogen or an organic radical having from 1 to 40 carbon atoms or two adjacent radicals $R^9$, $R^{10}$, $R^{11}$ or $R^{12}$ together with the atoms connecting them form a monocyclic or polycyclic ring system which may in turn be substituted, $R^{13}$, $R^{14}$ are identical or different and are each hydrogen or an organic radical having from 1 to 40 carbon atoms or $R^{13}$ and $R^{14}$ together with the atoms connecting them form a monocyclic or polycyclic ring system which may in turn be substituted, $R^{15}$, $R^{16}$, $R^{17}$ and $R^{18}$ are identical or different and are each hydrogen or an organic radical having from 1 to 40 carbon atoms or two adjacent radicals $R^{15}$, $R^{16}$, $R^{17}$ or $R^{18}$ together with the atoms connecting them form a monocyclic or polycyclic ring system which may in turn be substituted, $R^{19}$, $R^{20}$ are identical or different and are each hydrogen or an organic radical having from 1 to 40 carbon atoms or $R^{19}$ and $R^{20}$ together with the atoms connecting them form a monocyclic or polycyclic ring system which may in turn be substituted, $R^{21}$, $R^{22}$, $R^{23}$ and $R^{24}$ are identical or different and are each hydrogen or an organic radical having from 1 to 40 carbon atoms or two adjacent radicals $R^{21}$, $R^{22}$, $R^{23}$ or $R^{24}$ together with the atoms connecting them form a monocyclic or polycyclic ring system which may in turn be substituted, $R^{25}$, $R^{26}$ are identical or different and are each hydrogen or an organic radical having from 1 to 40 carbon atoms or $R^{25}$ and $R^{26}$ together with the atoms connecting them form a monocyclic or polycyclic ring system which may in turn be substituted, A' is a bridging structural element between the two substituted cyclopentadienyl ligands and may comprise, in addition to the atom or the two atoms which is/are bound directly to the two substituted cyclopentadienyl ligands, further radicals as substituents, the divalent groups E are identical or different and are each $BR^{27}$, $AlR^{27}$, $GaR^{27}$, $InR^{27}$, $Si(R^{27})_2$, $Ge(R^{27})_2$, $Sn(R^{27})_2$, O, S, Se, Te, $NR^{27}$, $PR^{27}$, $AsR^{27}$ or $SbR^{27}$, where the radicals $R^{27}$ are identical or different and are each hydrogen or an organic radical having from 1 to 40 carbon atoms, and at least one of the radicals $R^1$ to $R^{27}$ including the radicals of the bridging structural element A' is a monovalent olefinically unsaturated organic radical having from 2 to 40 carbon atoms.

M is an element of group 3, 4, 5 or 6 of the Periodic Table of the Elements or an element of the lanthanides, for example titanium, zirconium, hafnium, vanadium, niobium, tantalum, chromium, molybdenum or tungsten, preferably titanium, zirconium, hafnium, particularly preferably zirconium and hafnium, and especially preferably zirconium.

The radicals X are identical or different, preferably identical, and are each an organic or inorganic radical, with two radicals X also being able to be joined to one another. In particular, X is halogen, for example fluorine, chlorine, bromine, iodine, preferably chlorine, hydrogen, $C_1$-$C_{20}$-, preferably $C_1$-$C_4$-alkyl, $C_2$-$C_{20}$-, preferably $C_2$-$C_4$-alkenyl, $C_6$-$C_{22}$-, preferably $C_6$-$C_{10}$-aryl, an alkylaryl or arylalkyl group having from 1 to 10, preferably from 1 to 4, carbon atoms in the alkyl part and from 6 to 22, preferably from 6 to 10, carbon atoms in the aryl part, $-OR^d$ or $-NR^dR^e$, preferably $-OR^d$, with two radicals X also being able to be joined to one another, preferably two radicals $-OR^d$ which are each, in particular, a substituted or unsubstituted 1,1'-bi-2-phenoxide radical. Two radicals X can also form a substituted or unsubstituted diene ligand, in particular a 1,3-diene ligand. The radicals $R^d$ and $R^e$ are each $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl part and from 6 to 22, preferably from 6 to 10, carbon atoms in the aryl part. Very particular preference is given to X being chlorine or methyl.

The index m is 0, 1 or 2, with m+2 usually corresponding to the oxidation number of M, and m is usually preferably 2 in the case of the elements of group 4 of the Periodic Table of the Elements. When M is chromium, m is preferably 0 or 1, in particular 0.

The radical $R^1$ is hydrogen or an organic radical having from 1 to 40 carbon atoms. $R^1$ is preferably a cyclic, branched or unbranched $C_1$-$C_{20}$-, preferably $C_1$-$C_8$-alkyl radical, a $C_2$-$C_{20}$-, preferably $C_2$-$C_8$-alkenyl radical, an arylalkyl radical having from 1 to 10, preferably from 1 to, carbon atoms in the alkyl part and from 6 to 22, preferably from 6 to 10, carbon atoms in the aryl part or a $C_4$-$C_8$-heteroaromatic radical, with preferred heteroatoms being N, O, S and P, in particular O and S. Examples of particularly preferred radicals $R^1$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, thienyl, furyl, methylthienyl and methylfuryl, in particular methyl, ethyl and isopropyl.

The radical $R^2$ is hydrogen or an organic radical having from 1 to 40 carbon atoms. $R^2$ is preferably hydrogen, a cyclic, branched or unbranched $C_1$-$C_{20}$-, preferably $C_1$-$C_8$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^2$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl and 2-phenylethyl, in particular hydrogen, methyl, ethyl and isopropyl. $R^2$ is especially preferably hydrogen.

The radical $R^3$ is hydrogen or an organic radical having from 1 to 40 carbon atoms. $R^3$ is preferably hydrogen, a cyclic, branched or unbranched $C_1$-$C_{20}$-, preferably $C_1$-$C_8$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part or a $C_4$-$C_8$-heteroaromatic radical, with preferred heteroatoms being N, O, S and P, in particular O and S. Examples of particularly preferred radicals $R^3$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, thienyl, furyl, methylthienyl and methylfuryl, in particular methyl, ethyl and isopropyl.

The radical $R^4$ is hydrogen or an organic radical having from 1 to 40 carbon atoms. $R^4$ is preferably hydrogen, a cyclic, branched or unbranched $C_1$-$C_{20}$-, preferably $C_1$-$C_8$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part or a $C_4$-$C_8$-heteroaromatic radical, with preferred heteroatoms being N, O, S and P, in particular O and S. Examples of particularly preferred radicals $R^4$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, thienyl, furyl, methylthienyl and methylfuryl, in particular methyl, ethyl and isopropyl.

The radicals $R^3$ and $R^4$ can also together form a divalent group

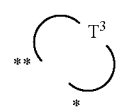

which is

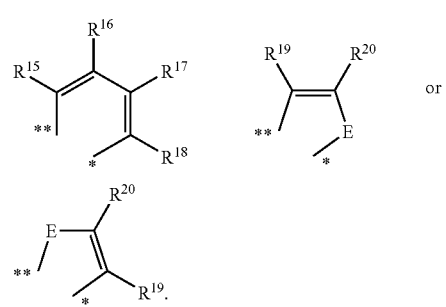

The radical $R^5$ is hydrogen or an organic radical having from 1 to 40 carbon atoms. $R^5$ is preferably hydrogen, a cyclic, branched or unbranched $C_1$-$C_{20}$-, preferably $C_1$-$C_8$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part or a $C_4$-$C_8$-heteroaromatic radical, with preferred heteroatoms being N, O, S and P, in particular O and S. Examples of particularly preferred radicals $R^5$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, thienyl, furyl, methylthienyl and methylfuryl, in particular methyl, ethyl and isopropyl.

The radical $R^8$ is hydrogen or an organic radical having from 1 to 40 carbon atoms. $R^6$ is preferably hydrogen, a cyclic, branched or unbranched $C_1$-$C_{20}$-, preferably $C_1$-$C_8$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part or a $C_4$-$C_8$-heteroaromatic radical, with preferred heteroatoms being N, O, S and P, in particular O and S. Examples of particularly preferred radicals $R^6$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, thienyl, furyl, methylthienyl and methylfuryl, in particular methyl, ethyl and isopropyl.

The radicals $R^5$ and $R^6$ can also together form a divalent group

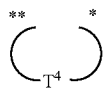

which is

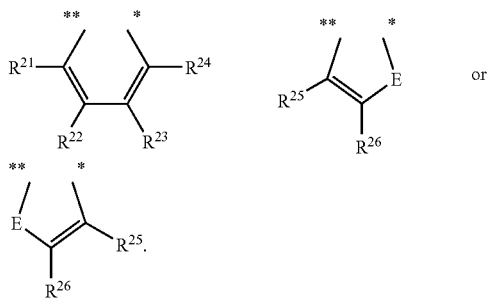

$R^7$, $R^8$ are identical or different and are each hydrogen or an organic radical having from 1 to 40 carbon atoms or $R^7$ and $R^8$ together with the atoms connecting them form a monocyclic or polycyclic ring system which may in turn be substituted.

$R^7$ is preferably hydrogen or a cyclic, branched or unbranched $C_1$-$C_{20}$-, preferably $C_1$-$C_{10}$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^7$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl and 2-phenylethyl, in particular hydrogen, methyl, ethyl and isopropyl, very particularly preferably methyl.

The radical $R^8$ is preferably hydrogen or an unsubstituted or alkyl-substituted $C_6$-$C_{40}$-aryl radical having from 1 to 10, preferably from 1 to 4, carbon atoms in the alkyl part and from 6 to 22, preferably from 6 to 10, carbon atoms in the aryl part, with the radicals also being able to be halogenated. Examples of preferred radicals $R^8$ are hydrogen, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl.

The radicals $R^7$ and $R^8$ which can also together form a cyclic ring system preferably form a substituted or unsubstituted, in particular unsubstituted, 1,3-butadiene-1,4-diyl group.

The radicals $R^9$, $R^{10}$, $R^{11}$ and $R^{12}$ are identical or different and are each hydrogen or an organic radical having from 1 to 40 carbon atoms or two adjacent radicals $R^9$, $R^{10}$, $R^{11}$ and $R^{12}$ together with the atoms connecting them form a monocyclic or polycyclic ring system which may in turn be substituted. Preference is given to the radicals $R^9$, $R^{10}$, $R^{11}$ and $R^{12}$ each being, independently of one another, hydrogen or a cyclic, branched or unbranched $C_1$-$C_{20}$-, preferably $C_1$-$C_{10}$-alkyl radical, a $C_2$-$C_{20}$-, preferably $C_2$-$C_8$-alkenyl radical, an aryl or alkylaryl or arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^9$, $R^{10}$, $R^{11}$ and $R^{12}$ are hydrogen, methyl, ethyl, n-propyl, isopropyl, n-butyl, i-butyl, s-butyl, n-pentyl, cyclopentyl, n-hexyl, cyclohexyl, n-heptyl, n-octyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, benzyl and 2-phenylethyl, in particular hydrogen, methyl, ethyl, isopropyl and t-butyl, very particularly preferably hydrogen.

The radicals $R^{13}$ and $R^{14}$ are identical or different and are each hydrogen or an organic radical having from 1 to 40 carbon atoms or $R^{13}$ and $R^{14}$ together with the atoms connecting them form a monocyclic or polycyclic ring system which may in turn be substituted, in which case they preferably form a substituted or unsubstituted, in particular unsubstituted 1,3-butadiene-1,4-diyl group. $R^{13}$ and $R^{14}$ are preferably each hydrogen or a cyclic, branched or unbranched $C_1$-$C_{20}$-, preferably $C_1$-$C_{10}$-alkyl radical, a $C_2$-$C_{20}$-, preferably $C_2$-$C_8$-alkenyl radical, an aryl or alkylaryl or arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^{13}$ and $R^{14}$ are hydrogen, methyl, ethyl, n-propyl, isopropyl, n-butyl, i-butyl, s-butyl, n-pentyl, cyclopentyl, n-hexyl, cyclohexyl, n-heptyl, n-octyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, benzyl and 2-phenylethyl, in particular hydrogen, methyl, ethyl, isopropyl and t-butyl, very particularly preferably hydrogen.

The radicals $R^{15}$, $R^{16}$, $R^{17}$ and $R^{18}$ are identical or different and are each hydrogen or an organic radical having from 1 to 40 carbon atoms or two adjacent radicals $R^{15}$, $R^{16}$, $R^{17}$ and $R^{18}$ together with the atoms connecting them form a monocyclic or polycyclic ring system which may in turn be substituted. Preference is given to the radicals $R^{15}$, $R^{16}$, $R^{17}$ and $R^{18}$ each being, independently of one another, hydrogen or a cyclic, branched or unbranched $C_1$-$C_{20}$-, preferably $C_1$-$C_{10}$- alkyl radical, a $C_2$-$C_{20}$-, preferably $C_2$-$C_8$-alkenyl radical, an aryl or alkylaryl or arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^{15}$, $R^{16}$, $R^{17}$ and $R^{18}$ are hydrogen, methyl, ethyl, n-propyl, isopropyl, n-butyl, i-butyl, s-butyl, n-pentyl, cyclopentyl, n-hexyl, cyclohexyl, n-heptyl, n-octyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, benzyl or 2-phenylethyl, in particular hydrogen, methyl, ethyl, isopropyl and t-butyl, very particularly preferably hydrogen.

The radicals $R^{19}$ and $R^{20}$ are identical or different and are each hydrogen or an organic radical having from 1 to 40 carbon atoms or $R^{19}$ and $R^{20}$ together with the atoms connecting them form a monocyclic or polycyclic ring system which may in turn be substituted, in which case they preferably form a substituted or unsubstituted, in particular unsubstituted, 1,3-butadiene-1,4-diyl group. $R^{19}$ and $R^{20}$ are preferably each hydrogen or a cyclic, branched or unbranched $C_1$-$C_{20}$-, preferably $C_1$-$C_{10}$-alkyl radical, a $C_2$-$C_{20}$-, preferably $C_2$-$C_8$-alkenyl radical, an aryl or alkylaryl or arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^{19}$ and $R^{20}$ are hydrogen, methyl, ethyl, n-propyl, isopropyl, n-butyl, i-butyl, s-butyl, n-pentyl, cyclopentyl, n-hexyl, cyclohexyl, n-heptyl, n-octyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, benzyl or 2-phenylethyl, in particular hydrogen, methyl, ethyl, isopropyl and t-butyl, very particularly preferably hydrogen.

The radicals $R^{21}$, $R^{22}$, $R^{23}$ and $R^{24}$ are identical or different and are each hydrogen or an organic radical having from 1 to 40 carbon atoms or two adjacent radicals $R^{21}$, $R^{22}$, $R^{23}$ and $R^{24}$ together with the atoms connecting them form a monocyclic or polycyclic ring system which may in turn be substituted. Preference is given to the radicals $R^{21}$, $R^{22}$, $R^{23}$ and $R^{24}$ each being, independently of one another, hydrogen or a cyclic, branched or unbranched $C_1$-$C_{20}$-, preferably $C_1$-$C_{10}$- alkyl radical, a $C_2$-$C_{20}$-, preferably $C_2$-$C_8$-alkenyl radical, an aryl or alkylaryl or arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^{21}$, $R^{22}$, $R^{23}$ and $R^{24}$ are hydrogen, methyl, ethyl, n-propyl, isopropyl, n-butyl, i-butyl, s-butyl, n-pentyl, cyclopentyl, n-hexyl, cyclohexyl, n-heptyl, n-octyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, benzyl and 2-phenylethyl, in particular hydrogen, methyl, ethyl, isopropyl and t-butyl, very particularly preferably hydrogen.

The radicals $R^{25}$ and $R^{26}$ are identical or different and are each hydrogen or an organic radical having from 1 to 40 carbon atoms or $R^{25}$ and $R^{26}$ together with the atoms connecting them form a monocyclic or polycyclic ring system which may in turn be substituted, in which case they preferably form a substituted or unsubstituted, in particular unsubstituted 1,3-butadiene-1,4-diyl group. $R^{25}$ and $R^{26}$ are preferably each hydrogen or a cyclic, branched or unbranched $C_1$-$C_{20}$-, preferably $C_1$-$C_{10}$-alkyl radical, a $C_2$-$C_{20}$-, preferably $C_2$-$C_8$- alkenyl radical, an aryl or alkylaryl or arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^{25}$ and $R^{26}$ are hydrogen, methyl, ethyl, n-propyl, isopropyl, n-butyl, i-butyl, s-butyl, n-pentyl, cyclopentyl, n-hexyl, cyclohexyl, n-heptyl, n-octyl, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-Dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl, benzyl or 2-phenylethyl, in particular hydrogen, methyl, ethyl, isopropyl and t-butyl, very particularly preferably hydrogen.

A' is a bridging structural element between the two substituted cyclopentadienyl ligands and may comprise, in addition to the atom or the two atoms which is/are bound directly to the two substituted cyclopentadienyl ligands, further radicals as substituents.

Examples of A' are:

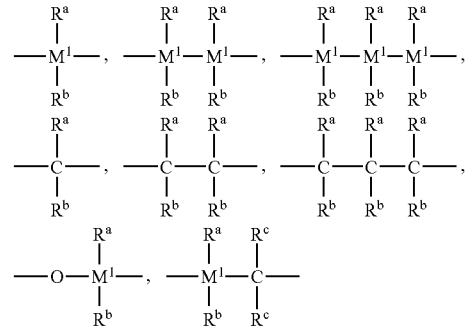

—B($R^a$)—, —B(N$R^a R^b$)—, —Al($R^a$)—, —O—, —S—, —S(O)—, —S($O_2$)—, —N($R^a$)—, —C(O)—, —P($R^a$)— or —P(O)($R^a$)—, preferably

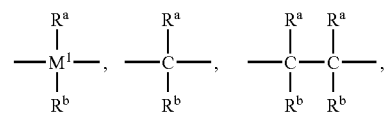

where $M^1$ is silicon, germanium or tin, preferably silicon or germanium, particularly preferably silicon, and $R^a$, $R^b$ and $R^c$ are identical or different and are each a hydrogen atom, a halogen atom, a trimethylsilyl group, a $C_1$-$C_{10}$, preferably $C_1$-$C_3$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-, preferably $C_1$-$C_3$-alkoxy group, a $C_7$-$C_{15}$-alkylaryloxy group, a $C_2$-$C_{10}$-, preferably $C_2$-$C_4$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms. A' is particularly preferably a substituted silylene group or a substituted ethylene group, in particular a substituted ethylene group.

The divalent groups E are identical or different, in particular identical, and are each $BR^{27}$, $AlR^{27}$, $GaR^{27}$, $InR^{27}$, $Si(R^{27})_2$, $Ge(R^{27})_2$, $Sn(R^{27})_2$, O, S, Se, Te, $NR^{27}$, $PR^{27}$, $AsR^{27}$ or $SbR^{27}$, in particular O, S or $NR^{27}$, where the radicals $R^{27}$ are identical or different and are each hydrogen or an organic radical having from 1 to 40 carbon atoms, in particular $C_1$-$C_{20}$-, preferably $C_{1-4}$-alkyl, $C_2$-$C_{20}$-, preferably $C_2$-$C_4$-alkenyl, $C_6$-$C_{22}$-, preferably $C_6$-$C_{10}$-aryl, an alkylaryl or arylalkyl group having from 1 to 10, preferably from 1 to 4, carbon atoms in the alkyl part and from 6 to 22, preferably from 6 to 10, carbon atoms in the aryl part. E is preferably S.

At least one of the radicals $R^1$ to $R^{21}$ including the radicals of the bridging structural element A', in particular one radical, is an olefinically unsaturated organic radical having from 2 to 40 carbon atoms, in particular an ω-alkeny radical, where an ω-alkenyl radical is a radical bearing a terminal vinyl group $CH_2=CH—$.

According to the invention, the radicals $R^1$ to $R^{27}$ may also contain, in place of carbon atoms or hydrogen atoms, further heteroatoms, in particular heteroatoms selected from the group consisting of Si, N, P, O, S, F and Cl, or functional groups which may also be modified by means of protective groups, without altering the polymerization properties of the novel organometallic transition metal compounds of the formula (I) or (II) as long as these heteroatoms or functional groups are chemically inert under the polymerization conditions.

Furthermore, the substituents according to the present invention are, unless restricted further, defined as follows:

The term "organic radical having from 1 to 40 carbon atoms" as used in the present text refers, for example, to $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic radical is in each case derived from an organic compound. Thus, the organic compound methanol can in principle give rise to three different organic radicals having 1 carbon atom, namely methyl ($H_3C—$), methoxy ($H_3C—O—$) and hydroxymethyl ($HOC(H_2)—$).

The term "alkyl" as used in the present text encompasses linear or singly or multiply branched saturated hydrocarbons which may also be cyclic. Preference is given to a $C_1$-$C_{18}$-alkyl such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present text encompasses linear or singly or multiply branched hydrocarbons having at least one C—C double bond, if appropriate a plurality of C—C double bonds which may be cumulated or conjugated.

The term "saturated heterocyclic radical" as used in the present text refers, for example, to monocyclic or polycyclic, substituted or unsubstituted hydrocarbon radicals in which one or more carbon atoms, CH groups and/or $CH_2$ groups are replaced by heteroatoms which are preferably selected from the group consisting of O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl-, propyl-, isopropyl- and tert-butyl-substituted derivatives thereof.

The term "aryl" as used in the present text refers to aromatic and, if appropriate, fused polyaromatic hydrocarbon substituents which may, if appropriate, be substituted by one or more linear or branched $C_1$-$C_{18}$-alkyl, $C_1$-$C_{18}$-alkoxy, $C_2$-$C_{10}$-alkenyl or $C_3$-$C_{15}$-alkylalkenyl groups. Preferred examples of substituted and unsubstituted aryl radicals are, in particular, phenyl, 4-methylphenyl, 4-ethylphenyl, 4-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present text refers to aromatic hydrocarbon substituents in which one or more carbon atoms are replaced by nitrogen, phosphorus, oxygen or sulfur atoms or combinations thereof. These may, like the aryl radicals, be substituted if appropriate by one or more linear or branched $C_1$-$C_{18}$-alkyl, $C_2$-$C_{10}$-alkenyl or $C_3$-$C_{15}$-alkylalkenyl groups. Preferred examples are furyl, thienyl, pyridyl, pyrazolyl, imidazolyl, oxazolyl, thiazolyl, pyrimidinyl, pyrazinyl and the like, and also methyl-, ethyl-, propyl-, isopropyl- and tert-butyl-substituted derivatives thereof.

The term "arylalkyl" as used in the present text refers to aryl-containing substituents whose aryl radical is bound via an alkyl chain to the remainder of the molecule. Preferred examples are benzyl, substituted benzyl, phenethyl, substituted phenethyl and the like.

The expressions fluoroalkyl and fluoroaryl mean that at least one hydrogen atom, preferably a plurality of hydrogen atoms up to all hydrogen atoms, of the respective substituent have been replaced by fluorine atoms. Examples of fluorine-containing substituents which are preferred according to the invention are trifluoromethyl, 2,2,2-trifluoroethyl, pentafluorophenyl, 4-trifluoromethylphenyl, 4-perfluoro-tert-butylphenyl and the like.

Particular preference is given to organometallic transition metal compounds of the formula (II)

in which

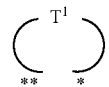

is a divalent group

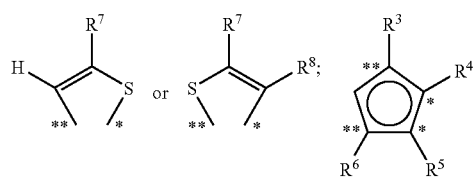

is a molecule fragment

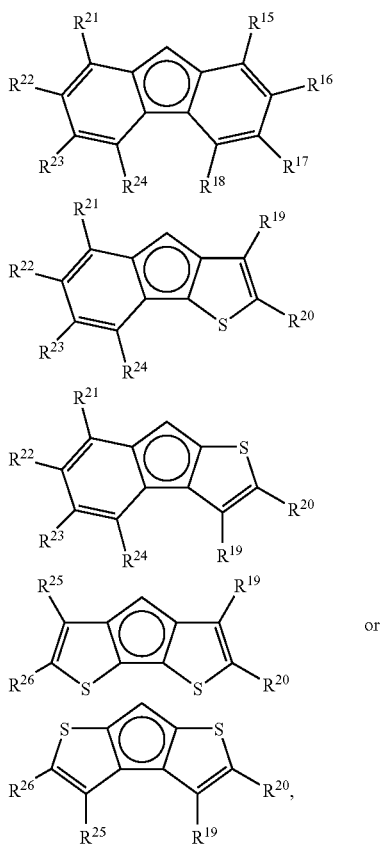

M is an element of group 4 of the Periodic Table of the Elements,
m is 2,
$R^1$ is an organic radical having from 1 to 40 carbon atoms,
$R^2$ is hydrogen,
$R^7$ is an organic radical having from 1 to 40 carbon atoms,
$R^8$ is hydrogen or an organic radical having from 1 to 40 carbon atoms or $R^7$ and $R^8$ together with the atoms connecting them form a monocyclic or polycyclic ring system which may in turn be substituted,
A' is

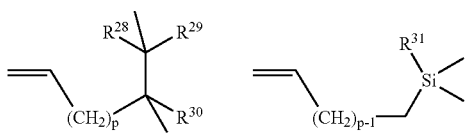

where $R^{28}$, $R^{29}$, $R^{30}$ and $R^{31}$ are identical or different and are each hydrogen or an organic radical having from 1 to 40 carbon atoms or two radicals $R^{28}$, $R^{29}$ and $R^{30}$ together with the atoms connecting them form a monocyclic or polycyclic ring system which may in turn be substituted, p is from 2 to 8, and the other variables are as defined for the formula (II).

M is an element of group 4 of the Periodic Table of the Elements, preferably zirconium or hafnium, particularly preferably zirconium.

The radical $R^1$ is an organic radical having from 1 to 40 carbon atoms. $R^1$ is preferably a cyclic, branched or unbranched $C_1$-$C_{20}$-, preferably $C_1$-$C_8$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part or a $C_4$-$C_8$-heteroaromatic radical, with preferred heteroatoms being N, O, S and P, in particular O and S. Examples of particularly preferred radicals $R^1$ are hydrogen, methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl, 2-phenylethyl, thienyl, furyl, methylthienyl and methylfuryl, in particular methyl, ethyl and isopropyl.

$R^7$ is an organic radical having from 1 to 40 carbon atoms, in particular a cyclic, branched or unbranched $C_1$-$C_{20}$-, preferably $C_1$-$C_{10}$-alkyl radical, a $C_2$-$C_{20}$-, preferably $C_2$-$C_8$-alkenyl radical, an arylalkyl radical having from 1 to 10, preferably from 1 to 4, carbon atoms in the alkyl part and from 6 to 22, preferably from 6 to 10, carbon atoms in the aryl part. Examples of particularly preferred radicals $R^7$ are methyl, ethyl, n-propyl, isopropyl, n-butyl, i-butyl, s-butyl, t-butyl, n-pentyl, cyclopentyl, n-hexyl, cyclohexyl, n-heptyl, n-octyl, benzyl and 2-phenylethyl, in particular methyl, ethyl and isopropyl, very particularly preferably methyl.

The radical $R^8$ is hydrogen or an organic radical having from 1 to 40 carbon atoms, in particular hydrogen or an unsubstituted or alkyl-substituted $C_6$-$C_{40}$-aryl radical having from 1 to 10, preferably from 1 to 4, carbon atoms in the alkyl part and from 6 to 22, preferably from 6 to 10, carbon atoms in the aryl part, with the radicals also being able to be halogenated. Examples of preferred radicals $R^8$ are hydrogen, phenyl, 2-tolyl, 3-tolyl, 4-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,5-di(tert-butyl)phenyl, 2,4,6-trimethylphenyl, 2,3,4-trimethylphenyl, 1-naphthyl, 2-naphthyl, phenanthryl, p-isopropylphenyl, p-tert-butylphenyl, p-s-butylphenyl, p-cyclohexylphenyl and p-trimethylsilylphenyl.

The radicals $R^7$ and $R^8$ which together with the atoms connecting them may also form a monocyclic or polycyclic ring system preferably form a substituted or unsubstituted, in particular unsubstituted, 1,3-butadiene-1,4-diyl group.

A' is

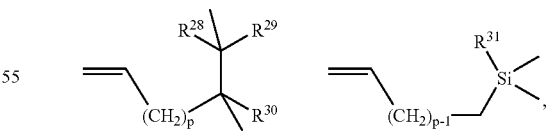

where $R^{28}$, $R^{29}$, $R^{30}$ and $R^{31}$ are identical or different and are each hydrogen or an organic radical having from 1 to 40 carbon atoms, preferably a $C_1$-$C_4$-alkyl or $C_6$-$C_{10}$-aryl radical, or two radicals $R^{28}$, $R^{29}$ and $R^{30}$, in particular $R^{28}$ and $R^{29}$, or $R^{28}$ and $R^{30}$, together with the atoms connecting them form a monocyclic or polycyclic, substituted or unsubstituted ring system, in particular a cyclohexane ring system.

$R^{28}$, $R^{29}$ and $R^{30}$ are preferably each hydrogen, $C_1$-$C_4$-alkyl or $C_6$-$C_{10}$-aryl, in particular hydrogen.

$R^{31}$ is preferably a $C_1$-$C_4$-alkyl or $C_6$-$C_{10}$-aryl radical, in particular methyl or phenyl.

p is from 2 to 8, in particular from 2 to 6.

Illustrative examples of the novel organmetallic transition metal compounds of the formula (I) or (II) which do not, however, restrict the scope of the invention are:

8-$\eta^5$-[2-(3-methylcyclopenta[b]benzothienylidene)]-7-$\eta^5$-(9-fluorenylidene)-1-octenezirconium dichloride 7-$\eta^5$-[2-(3-methylcyclopenta[b]benzothienylidene)]-8-$\eta^5$-(9-fluorenylidene)-1-octenezirconium dichloride 8-$\eta^5$-[6-(5-methylcyclopenta[b]thienylidene)]-7-$\eta^5$-(9-fluorenylidene)-1-octenezirconium dichloride 8-$\eta^5$-[6-(2,5-dimethylcyclopenta[b]thienylidene)]-7-$\eta^5$-(9-fluorenylidene)-1-octenezirconium dichloride 8-$\eta^5$-[6-(2,4,5-trimethylcyclopenta[b]thienylidene)]-7-$\eta^5$-(9-fluorenylidene)-1-octenezirconium dichloride 8-$\eta^5$-[6-(2,3,4,5-tetramethylcyclopenta[b]thienylidene)]-7-$\eta^5$-(9-fluorenylidene)-1-octenezirconium dichloride 8-$\eta^5$-[6-(3-phenyl-2,5-dimethylcyclopenta[b]thienylidene)]-7-$\eta^5$-(9-fluorenylidene)-1-octenezirconium dichloride 8-$\eta^5$-[6-(5-isopropylcyclopenta[b]thienylidene)]-7-$\eta^5$-(9-fluorenylidene)-1-octenezirconium dichloride 6-$\eta^5$-[6-(5-methylcyclopenta[b]thienylidene)]-5-$\eta^5$-(9-fluorenylidene)-1-hexenezirconium dichloride 6-$\eta^5$-[6-(3-phenyl-2,5-dimethylcyclopenta[b]thienylidene)]-5-$\eta^5$-(9-fluorenylidene)-1-hexenezirconium dichloride 8-$\eta^5$-[6-(5-methylcyclopenta[b]thienylidene)]-7-$\eta^5$-[4-(2-methylindeno[b]thienylidene)]-1-octenezirconium dichloride 8-$\eta^5$-[6-(2,4,5-methylcyclopenta[b]thienylidene)]-7-$\eta^5$-[4-(2-methylindeno[b]thienylidene)]-1-octenezirconium dichloride 8-$\eta^5$-[6-(2,5-methylcyclopenta[b]thienylidene)]-7-$\eta^5$-[4-cyclopenta[def]phenathrylidene)]-1-octenezirconium dichloride 1-$\eta^5$-[6-(4-(hept-6-enyl)-2,5-dimethylcyclopenta[b]thienylidene)]-2-$\eta^5$-[1-(2-methyl-9-thiacyclopenta[b]fluorenylidene]ethanezirconium dichloride 8-$\eta^5$-[6-(2-(hept-6-enyl)-5-methylcyclopenta[b]thienylidene)]-7-$\eta^5$-(9-fluorenylidene)-1-octenezirconium dichloride 7-$\eta^5$-(11-benzo[b]fluorenylidene)-8-$\eta^5$-[6-(2,5-dimethylcyclopenta[b]thienylidene)]-1-octenezirconium dichloride 7-$\eta^5$-[6-(2,5-dimethylcyclopenta[b]thienylidene)]-7-$\eta^5$-(9-fluorenylidene)-1-octenezirconium dichloride 2-$\eta^5$-(9-fluorenylidene)-2-$\eta^5$-[6-(2-(hex-6-enyl)-5-methylcyclopenta[b]thienylidene)]-propanezirconium dichloride 8-$\eta^5$-[6-(2,5-dimethylcyclopenta[b]thienylidene)]-7-$\eta^5$-[9-(3,6-di-tert-butyl)fluorenylidene]-1-octenezirconium dichloride 1-$\eta^5$-[6-(5-methylcyclopenta[b]thienylidene)]-2-$\eta^5$-[9-(2,7-di(oct-7-enyl)fluorenylidene)]ethanezirconium dichloride.

The naming of the abovementioned compounds according to the invention will be illustrated with the aid of the compound 8-$\eta^5$-[2-(3-methylcyclopenta[b]benzothienylidene)]-7-$\eta^5$-(9-fluorenylindene)-1-octenezirconium dichloride

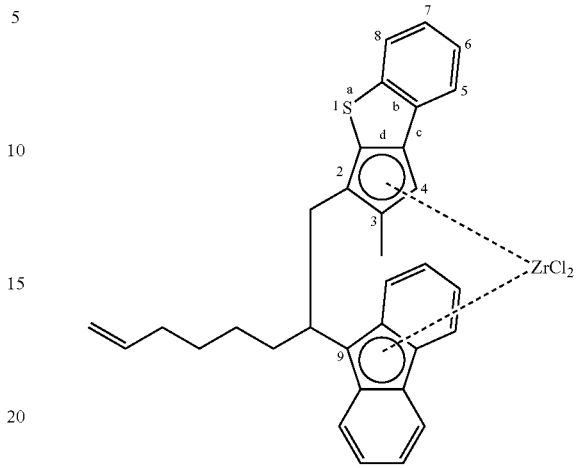

and the compound

8-$\eta^5$-[6-(3-methylcyclopenta[b]thienylidene)]-7-$\eta^5$-[4-(2-methylindeno[b]thienylidene)]-1-octenezirconium dichloride

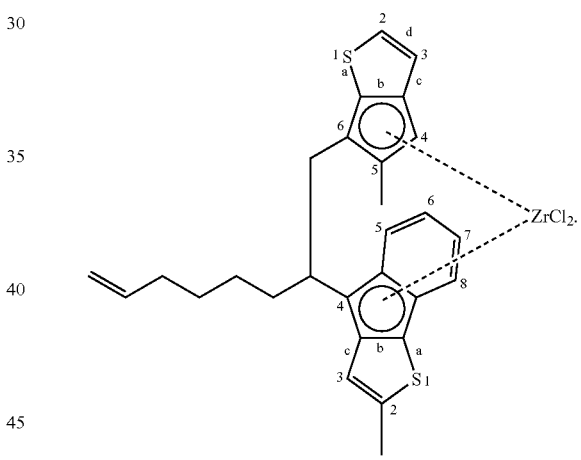

The novel organometallic transition metal compounds of the formula (I) or (II) when used in the homopolymerization of ethylene give a polyethylene having a high molar mass and a defined chain structure depending on the molecular weight. The polyethylenes also have narrow molar mass distributions.

The novel organometallic transition metal compounds of the formula (I) or (II) can be prepared by methods as described in Journal of Organometallic Chemistry 580, (1999), 1 to 16, and in WO 01/47939.

In the majority of cases, the organometallic transition metal compounds of the formula (I) or (II) are obtained as mixtures of isomers, i.e. as mixtures of diastereomers and/or mixtures of regioisomers, which can be used directly for preparing a catalyst without further separation into the individual isomers. Of course, it is also possible to use an individual isomer of the novel organometallic transition metal compounds of the formula (I) or (II) in the preparation of a catalyst and the subsequent polymerization process. Preference is given to using the isomer mixture obtained in the synthesis of the novel organometallic transition metal compounds of the formula (I) or (II) for preparing the catalyst.

The invention further provides a bridged ligand system of the formula (III)

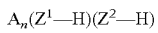

$A_n(Z^1—H)(Z^2—H)$ (III)

where n=1 and the variables A, $Z^1$ and $Z^2$ are as defined for the formula (I).

Preference is given to a ligand system of the formula (IV)

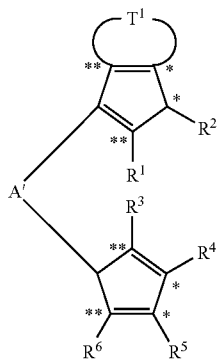

or its double bond isomers, where the variables $T^1$, $R^1$, $R^2$, $R^3$, $R^4$, $R^5$, $R^6$ and A' are as defined for the formula (II).

The double bond isomers of the compound of the formula (IV) result from a formal shift of the double bonds in the two five-membered rings.

Particular preference is given to a ligand system of the formula (IV) or its double bond isomers in which

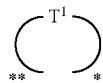

is a divalent group

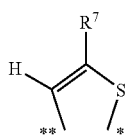 or 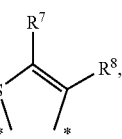, 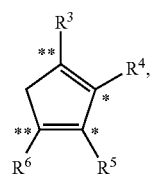

is a molecule fragment

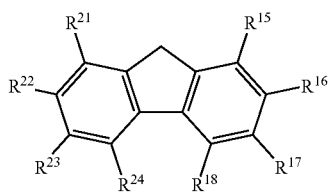

-continued

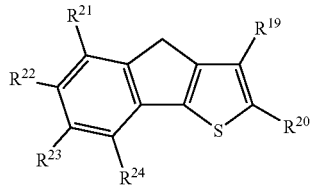

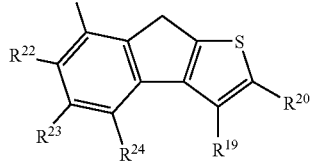

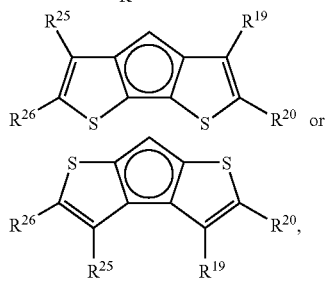

$R^1$ is an organic radical having from 1 to 40 carbon atoms,
$R^2$ is hydrogen,
$R^7$ is an organic radical having from 1 to 40 carbon atoms,
$R^8$ is hydrogen or an organic radical having from 1 to 40 carbon atoms or $R^7$ and $R^8$ together with the atoms connecting them form a monocyclic or polycyclic ring system which may in turn be substituted,
A' is

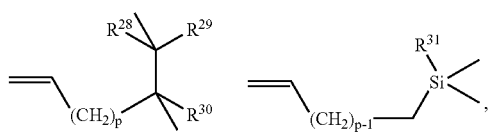

where $R^{28}$, $R^{29}$, $R^{30}$ and $R^{31}$ are identical or different and are each hydrogen or an organic radical having from 1 to 40 carbon atoms or two radicals $R^{28}$, $R^{29}$ and $R^{30}$ together with the atoms connecting them form a monocyclic or polycyclic ring system which may in turn be substituted, p is from 2 to 8, and the other variables are as defined for the formula (II).

The substitution pattern of the ligand systems of the formulae (III) and (IV) is critical to the particular polymerization properties of the organometallic transition metal compounds containing these ligand systems.

The novel bridged ligand systems of the formula (III) or (IV) can be prepared by methods known from the literature or as described in the experimental metal part.

In their preparation, the bridged ligand systems of the formula (III) or (IV) can, depending on the starting materials used, be obtained as mixtures of isomers, i.e. as a mixture of enantiomers, a mixture of diastereomers and/or a mixture of regioisomers, which can be used directly for preparing the organometallic transition metal compounds of the invention without further separation into the individual isomers.

Of course, it is also possible to use an individual isomer of the novel organometallic transition metal compounds of the formula (I) or (II) in the preparation of a catalyst and the subsequent polymerization process. Preference is given to using the mixture of isomers obtained in the synthesis for preparing the catalyst.

The invention further provides for the use of a ligand system of the formula (III) or (IV) for preparing an organometallic transition metal compound, preferably for preparing an organometallic transition metal compound of an element of group 4 of the Periodic Table of the Elements, in particular zirconium.

The present invention therefore also provides a process for preparing an organometallic transition metal compound, which comprises reacting a ligand system of the formula (III) or (IV) or a bisanion prepared therefrom with a transition metal compound. Usually, a ligand system of the formula (III) or (IV) is firstly doubly deprotonated by means of a base such as n-butyllithium and subsequently reacted with a suitable transition metal source, for example zirconium tetrachloride. However, as an alternative, the uncharged ligand system of the formula (III) or (IV) can be reacted directly with a suitable transition metal source which has strongly basic ligands, for example tetrakis(dimethylamino)zirconium.

The novel organometallic transition metal compounds of the formula (I) or (II) are, particularly in the presence of suitable cocatalysts, highly active catalyst constituents for the polymerization, i.e. homopolymerization or copolymerization, of olefins, in particular of α-olefins such as ethylene, propene or butene. The novel organometallic transition metal compounds of the formula (I) or (II) are particularly useful as constituents of catalyst systems for the homopolymerization and copolymerization of ethylene. In the case of copolymerization, preference is given to using propene, 1-butene, 1-hexene and/or 1-octene as comonomers.

The cocatalyst which together with the novel organometallic transition metal compound of the formula (I) or (II) forms a polymerization-active catalyst system is able to convert the organometallic transition metal compound into a species which displays polymerization activity toward at least one olefin. The cocatalyst is therefore sometimes also referred to as activating compound. The polymerization-active transition metal species is frequently a cationic species. In this case, the cocatalyst is frequently also referred to as cation-forming compound.

The present invention therefore also provides a catalyst system for the polymerization of olefins comprising at least one organometallic transition metal compound of the formula (I) or (II) and at least one cocatalyst which is able to convert the organometallic transition metal compound into a species which displays polymerization activity toward at least one olefin.

Suitable cocatalysts or cation-forming compounds are, for example, compounds such as an aluminoxane, a strong uncharged Lewis acid, an ionic compound having a Lewis-acid cation or an ionic compound containing a Brönsted acid as cation. Preference is given to using an aluminoxane as cocatalyst.

In the case of metallocene complexes as organometallic transition metal compound, the cocatalysts are frequently also referred to as compounds capable of forming metallocenium ions.

As aluminoxanes, it is possible to use, for example, the compounds described in WO 00/31090. Particularly useful compounds are open-chain or cyclic aluminoxane compounds of the general formula (V) or (VI)

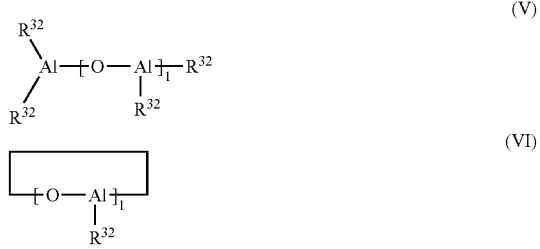

where
$R^{32}$ is a $C_1$-$C_4$-alkyl group, preferably a methyl or ethyl group, and I is an integer from 5 to 30, preferably from 10 to 25.

These oligomeric aluminoxane compounds are usually prepared by reacting a solution of trialkylaluminum with water. In general, the oligomeric aluminoxane compounds obtained in this way are in the form of mixtures of both linear and cyclic chain molecules of various lengths, so that m is to be regarded as a mean. The aluminoxane compounds can also be present in admixture with other metal alkyls, preferably aluminum alkyls.

Furthermore, it is also possible to use modified aluminoxanes in which some of the hydrocarbon radicals or hydrogen atoms have been replaced by alkoxy, aryloxy, siloxy or amide radicals in place of the aluminoxane compounds of the general formula (V) or (VI).

It has been found to be advantageous to use the novel organometallic transition metal compound of the formula (I) or (II) and the aluminoxane compounds in such amounts that the atomic ratio of aluminum from the aluminoxane compounds to the transition metal from the organometallic transition metal compound is in the range from 10:1 to 1000:1, preferably in the range from 20:1 to 500:1 and in particular in the range from 30:1 to 400:1.

As strong, uncharged Lewis acids, preference is given to compounds of the general formula (VII)

where
$M^2$ is an element of group 13 of the Periodic Table of the Elements, in particular B, Al or Ga, preferably B,
$X^1$, $X^2$ and $X^3$ are each, independently of one another, hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl part and from 6 to 20 carbon atoms in the aryl part or fluorine, chlorine, bromine or iodine, in particular haloaryl, preferably pentafluorophenyl.

Further examples of strong, uncharged Lewis acids are given in WO 00/31090.

Particular preference is given to compounds of the general formula (VII) in which $X^1$, $X^2$ and $X^3$ are identical, preferably tris(pentafluorophenyl)borane.

Strong uncharged Lewis acids which are suitable as cocatalysts or cation-forming compounds also include the reaction products from the reaction of a boronic acid with two equivalents of a trialkylaluminum or the reaction products from the reaction of a trialkylaluminum with two equivalents of an acidic fluorinated, in particular perfluorinated, hydrocarbon compound such as pentafluorophenol or bis(pentafluorophenyl)boronic acid.

Suitable ionic compounds having Lewis-acid cations include salt-like compounds of the cation of the general formula (VIII)

where
Y is an element of groups 1 to 16 of the Periodic Table of the Elements,
$Q^1$ to $Q^z$ are singly negatively charged radicals such as $C_1$-$C_{28}$-alkyl, $C_6$-$C_{15}$-aryl, alkylaryl, arylalkyl, haloalkyl, haloaryl each having from 6 to 20 carbon atoms in the aryl part and from 1 to 28 carbon atoms in the alkyl part, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups,
a is an integer from 1 to 6 and
z is n integer from 0 to 5, and
d corresponds to the difference a-z, but d is greater than or equal to 1.

Particularly useful Lewis-acid cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react so as to link two or more boron or aluminum atoms, e.g. water, and a third compound which reacts with the boron or aluminum compound to form an ionizing ionic compound, e.g. triphenylchloromethane. In addition, a fourth compound which likewise reacts with the boron or aluminum compound, e.g. pentafluorophenol, can also be added.

Ionic compounds containing Brönsted acids as cations preferably likewise have noncoordinating counterions. As Brönsted acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Preferred ionic compounds as cocatalysts or cation-forming compounds are, in particular, N,N-dimethylanilinium tetrakis(pentafluorophenyl)borate, N,N-dimethylcyclohexylammonium tetrakis(pentafluorophenyl)borate or N,N-dimethylbenzylammonium tetrakis(pentafluorophenyl)borate.

It is also possible for two or more borate anions to be joined to one another as in the dianion [$(C_6F_5)_2$B—$C_6F_4$—B$(C_6F_5)_2$]$^{2-}$, or the borate anion can be bound via a bridge having a suitable functional group to the surface of a support particle.

Further suitable cocatalysts or cation-forming compounds are listed in WO 00/31090.

The amount of strong, uncharged Lewis acids, ionic compounds having Lewis-acid cations or ionic compounds containing Brönsted acids as cations is usually from 0.1 to 20 equivalents, preferably from 1 to 10 equivalents, based on the novel organometallic transition metal compound of the formula (I) or (II).

Further suitable cocatalysts or cation-forming compounds are boron-aluminum compounds such as di[bis(pentafluorophenylboroxy)]methylalane. Boron-aluminum compounds of this type are disclosed, for example, in WO 99/06414.

It is also possible to use mixtures of all the abovementioned cocatalysts or cation-forming compounds. Preferred mixtures comprise aluminoxanes, in particular methylaluminoxane, and an ionic compound, in particular a compound containing the tetrakis(pentafluorophenyl)borate anion, and/or a strong uncharged Lewis acid, in particular tris(pentafluorophenyl)borane.

Both the novel organometallic transition metal compound of the formula (I) or (II) and the cocatalysts or cation-forming compounds are preferably used in a solvent, preferably an aromatic hydrocarbon having from 6 to 20 carbon atoms, in particular xylenes and toluene.

In addition, the catalyst can further comprise a metal compound of the general formula (IX),

where
$M^3$ is an alkali metal, an alkaline earth metal or a metal of group 13 of the Periodic Table, i.e. boron, aluminum, gallium, indium or thallium,
$R^{33}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part,
$R^{34}$ and $R^{35}$ are identical or different and are each hydrogen, halogen, $C_1$-$C_{10}$-alkyl, $C_6$-$C_{15}$-aryl, alkylaryl, arylalkyl or alkoxy each having from 1 to 10 carbon atoms in the alkyl part and from 6 to 20 carbon atoms in the aryl part,
r is an integer from 1 to 3,
and
and t are integers from 0 to 2, with the sum r+s+t corresponding to the valence of $M^3$, where the metal compound of the formula (IX) is usually not identical to the cocatalyst or the cation-forming compound. It is also possible to use mixtures of various metal compounds of the formula (IX).

Among the metal compounds of the general formula (IX), preference is given to those in which $M^3$ is lithium, magnesium or aluminum and $R^{34}$ and $R^{35}$ are each $C_1$-$C_{10}$-alkyl.

Particularly preferred metal compounds of the formula (IX) are n-butyllithium, n-butyl-n-octylmagnesium, n-butyl-n-heptylmagnesium, isoprenylaluminum, tri-n-hexylaluminum, triisobutylaluminum, triethylaluminum and trimethylaluminum and mixtures thereof.

When a metal compound of the formula (IX) is used, it is preferably present in the catalyst in such an amount that the molar ratio of $M^3$ from the formula (IX) to transition metal M from the novel organometallic transition metal compound of the formula (I) or (II) is from 800:1 to 1:1, in particular from 200:1 to 2:1.

Particular preference is given to a catalyst system comprising at least one novel organometallic transition metal compound of the formula (I) or (II) and at least one cocatalyst and, in addition, a support.

To obtain such a supported catalyst system, the unsupported catalyst system can be reacted with a support. In principle, the order in which the support, the organometallic transition metal compound of the invention and the cocatalyst are combined is immaterial. The organometallic transition metal compound of the invention and the cocatalyst can be immobilized independently of one another or simultaneously. After the individual process steps, the solid can be washed with suitable inert solvents such as aliphatic or aromatic hydrocarbons.

As supports, preference is given to using finely divided supports which can be any organic or inorganic, inert solid. In particular, the support can be a porous solid such as talc, a sheet silicate, an inorganic oxide or a finely divided polymer powder (e.g. polyolefin).

Suitable inorganic oxides may be found in groups 2, 3, 4, 5, 13, 14, 15 and 16 of the Periodic Table of the Elements. Examples of oxides preferred as supports include silicon dioxide, aluminum oxide and also mixed oxides of the elements calcium, aluminum, silicon, magnesium or titanium and also corresponding oxide mixtures. Other inorganic oxides which can be used alone or in combination with the abovementioned preferred oxidic supports are, for example, MgO, $ZrO_2$, $TiO_2$ or $B_2O_3$. A preferred mixed oxide is, for example, calcined hydrotalcite.

The support materials used preferably have a specific surface area in the range from 10 to 1000 m²/g, a pore volume in the range from 0.1 to 5 ml/g and a mean particle size of from 1 to 500 µm. Preference is given to supports having a specific surface area in the range from 50 to 500 m²/g, a pore volume in the range from 0.5 to 3.5 ml/g and a mean particle size in the range from 5 to 350 µm. Particular preference is given to supports having a specific surface area in the range from 200 to 400 m²/g, a pore volume in the range from 0.8 to 3.0 ml/g and a mean particle size of from 10 to 100 µm.

The inorganic support can be subjected to a thermal treatment, e.g. to remove adsorbed water. Such a drying treatment is generally carried out at temperatures in the range from 80° C. to 300° C., preferably from 100° C. to 200° C., with drying at from 100° C. to 200° C. preferably being carried out under reduced pressure and/or under a blanket of inert gas (e.g. nitrogen), or the inorganic support can be calcined at temperatures of from 200° C. to 1000° C. to produce the desired structure of the solid and/or set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, treatment of silica gel with $(NH_4)_2SiF_6$ leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. supports based on polystyrenes, via whose functional groups, for example ammonium or hydroxy groups, at least one of the catalyst components can be fixed.

In a preferred embodiment of the preparation of the supported catalyst system, at least one of the novel organometallic transition metal compounds of the formula (I) or (II) is/are usually brought into contact with at least one cocatalyst as activating or cation-forming compound in a suitable solvent, to give a soluble or insoluble, preferably soluble, reaction product, an adduct or a mixture. The preparation obtained in this way is then mixed with the dehydrated or passivated support material, the solvent is removed and the resulting supported organometallic transition metal compound catalyst system is dried to ensure that all or most of the solvent is removed from the pores of the support material. The supported catalyst is obtained as a free-flowing powder. Examples of the industrial implementation of the above process are described in WO 96/00243, WO 98/40419 or WO 00/05277.

A further preferred embodiment comprises firstly applying the cocatalyst or the cation-forming compound to the support component and subsequently bringing this supported cocatalyst or cation-forming compound into contact with the organometallic transition metal compound of the invention.

Suitable cocatalyst systems therefore likewise include combinations obtained by combining the following components:

1st component: at least one defined boron or aluminum compound,
2nd component: at least one uncharged compound which has at least one acidic hydrogen atom,
3rd component: at least one support, preferably an inorganic oxidic support, and optionally, as 4th component, a base, preferably an organic nitrogen-containing base, for example an amine, an aniline derivative or a nitrogen heterocycle.

The boron or aluminum compounds used in the preparation of the supported cocatalysts are preferably compounds of the formula (X)

where the radicals
$R^{36}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, or $R^{36}$ is an $OSiR^{37}_3$ group, where the radicals
$R^{37}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, preferably hydrogen, $C_1$-$C_6$-alkyl or $C_7$-$C_{20}$-arylalkyl, and
$M^4$ is boron or aluminum, preferably aluminum.

Particularly preferred compounds of the formula (X) are trimethylaluminum, triethylaluminum and triisobutylaluminum.

The uncharged compounds which have at least one acidic hydrogen atom and can react with compounds of the formula (X) are preferably compounds of the formulae (XI), (XII) or (XIII),

$$R^{38}-D-H \quad (XI)$$
$$(R^{38})_{3-h}-B-(D-H)_h \quad (XII)$$
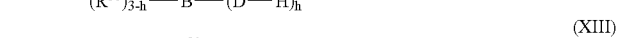
$$H-D-R^{39}-D-H \quad (XIII)$$

where the radicals
$R^{38}$ are identical or different and are each hydrogen, halogen, a boron-free organic group having from 1 to 40 carbon atoms, e.g. $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalky, $C_7$-$C_{40}$-haloarylalky, $C_7$-$C_{40}$-alkylaryl, $C_7$-$C_{40}$-haloalkylaryl, an $Si(R^{40})_3$ group or a $CH(SiR^{40}_3)_2$ group, where
$R^{40}$ is a boron-free organic group having from 1 to 40 carbon atoms, e.g. $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalky, $C_2$-$C_{40}$-haloarylalky, $C_7$-$C_{40}$-alkylaryl, $C_2$-$C_{40}$-haloalkylaryl, and
$R^{39}$ is a divalent organic group having from 1 to 40 carbon atoms, e.g. $C_1$-$C_{20}$-alkylene, $C_1$-$C_{20}$-haloalkylene, $C_6$-$C_{20}$-arylene, $C_6$-$C_{20}$-haloarylene, $C_7$-$C_{40}$-arylalkylene, $C_7$-$C_{40}$-haloarylalkylene, $C_7$-$C_{40}$-alkylarylene, $C_7$-$C_{40}$-haloalkylarylene,
D is an element of group 16 of the Periodic Table of the Elements or an $NR^{41}$ group, where $R^{41}$ is hydrogen or a $C_1$-$C_{20}$-hydrocarbon radical such as $C_1$-$C_{20}$-alkyl or $C_6$-$C_{20}$-aryl, with D preferably being oxygen, and
h is 1 or 2.

Suitable compounds of the formula (XI) are water, alcohols, phenol derivatives, thiophenol derivatives or aniline derivatives, with halogenated and in particular perfluorinated alcohols and phenols being of particular importance. Examples of particularly useful compounds are pentafluorophenol, 1,1-bis(pentafluorophenyl)methanol and 4-hydroxy-2,2',3,3',4',5,5',6,6'-nonafluorobiphenyl. Suitable compounds of the formula (XII) include boronic acids and borinic acids, with borinic acids bearing perfluorinated aryl radicals, for example $(C_6F_5)_2BOH$, being worthy of particular mention. Suitable compounds of the formula (XIII)

include dihydroxy compounds in which the divalent hydrocarbon group is preferably halogenated and in particular perfluorinated. An example of such a compound is 4,4'-dihydroxy-2,2',3,3',5,5',6,6'-octafluorobiphenyl hydrate.

Examples of combinations of compounds of the formula (X) with compounds of the formula (XI) or (XIII) are trimethylaluminum/pentafluorophenol, trimethylaluminum/1-bis (pentafluorophenyl)methanol, trimethylaluminum/4-hydroxy-2,2',3,3',4',5,5',6,6'-nonafluorobiphenyl, triethylaluminum/pentafluorophenol and triisobutylaluminum/pentafluorophenol and triethylaluminum/4,4'-dihydroxy-2,2',3,3',5,5',6,6'-octafluorobiphenyl hydrate, with reaction products of, for example, the following type being able to be formed.

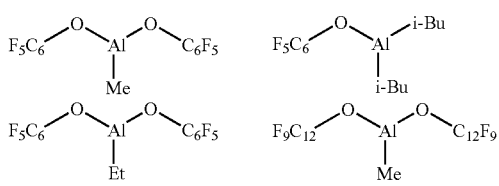

Examples of reaction products from the reaction of at least one compound of the formula (X) with at least one compound of the formula (XII) are:

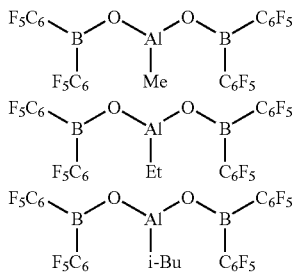

In principle, the components can be combined in any desired way.

If appropriate, the reaction products from the reaction of at least one compound of the formula (X) with at least one compound of the formula (XI), (XII) or (XIII) and optionally the organic nitrogen base are additionally combined with an organometallic compound of the formula (V), (VI), (VII) and/or (IX) in order then to form the supported cocatalyst system with the support.

In a preferred variant, the 1st component, e.g. compounds of the formula (X), is combined with the 2nd component, e.g. compounds of the formula (XI), (XII) or (XIII), and a support as 3rd component is combined separately with a base as 4th component and the two mixtures are subsequently reacted with one another, preferably in an inert solvent or suspension medium. The supported cocatalyst formed can be freed of the inert solvent or suspension medium before it is reacted with the novel organometallic transition metal compound of the formula (I) or (II) and, if appropriate, a metal compound of the formula (IX) to form the catalyst system.

It is also possible for the catalyst solid firstly to be prepolymerized with α-olefins, preferably linear $C_2$-$C_{10}$-1-alkenes and in particular ethylene or propene, and for the resulting prepolymerized catalyst solid then to be used in the actual polymerization. The mass ratio of catalyst solid used in the prepolymerization to monomer polymerized onto it is usually in the range from 1:0.1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the supported catalyst system. The molar ratio of additives to organometallic transition metal compound is usually from 1:1000 to 1000:1, preferably from 1:5 to 20:1.

The catalyst system of the invention comprising at least one novel organometallic transition metal compound of the formula (I) or (II), a suitable cocatalyst and possibly a support can be used alone or together with one or more further catalyst systems, which can likewise be supported and are suitable for the homopolymerization, copolymerization or oligomerization of olefins, in a polymerization process. In this case, the further catalyst system or systems can be prepared independently of the catalyst system of the invention or can be produced together with this. The different catalyst systems can, for example, be present together on a support or they can be present independently as supported or unsupported catalyst systems which are premixed in any desired way and thus introduced together or separately and thus independently into the polymerization reactor. Examples of known catalyst systems which can be used together with the catalyst system of the invention for preparing polyolefins are, in particular, classical Ziegler-Natta catalysts based on titanium, classical Phillips catalysts based on chromium oxides or single-site catalysts which preferably comprise, as transition metal component, metallocenes, viz. constrained geometry complexes (cf., for example, EPA 0 416 815 or EPA 0 420 436), chromium single-site complexes as are described, for example, in U.S. Pat. No. 6,437,161, nickel and palladium bisimine systems (which can be prepared as described in WO 9803559 A1) or iron and cobalt pyridinebisimine compounds (which can be prepared as described in WO 9827124 A1). If the catalyst system of the invention is used together with at least one further catalyst for the polymerization, preference is given to using a single-site catalyst, in particular one based on an iron pyridinebisimine compound.

The present invention also provides a process for preparing polyolefins by polymerization, i.e. homopolymerization or copolymerization, of at least one olefin in the presence of a catalyst system comprising at least one of the novel organometallic transition metal compounds of the formula (I) or (II).

In general, the catalyst system is used together with a further metal compound of the general formula (IX), which may be different from the metal compound or compounds of the formula (IX) used in the preparation of the catalyst system, for the polymerization or copolymerization of olefins. The further metal compound is generally added to the monomer or the suspension medium and serves to free the monomer of substances which could adversely affect the catalyst activity. It is also possible for one or more further cocatalytic or cation-forming compounds to be additionally added to the catalyst system in the polymerization process.

The olefins can be functionalized, olefinically unsaturated compounds such as ester or amide derivatives of acrylic or methacrylic acid, for example acrylates, methacrylates or acrylonitrile, or nonpolar olefinic compounds, including aryl-substituted α-olefins.

Preference is given to polymerizing olefins of the formula $R'''$—CH═CH—$R''$, where $R'''$ and $R''$ are identical or different and are each hydrogen or an organic radical having from 1 to 20 carbon atoms, in particular from 1 to 10 carbon atoms, or $R'''$ and $R''$ together with the atoms connecting them can form one or more rings.

Examples of such olefins are 1-olefins having from 2 to 40, preferably from 2 to 10, carbon atoms, e.g. ethylene, propylene, 1-butene, 1-pentene, 1-hexene, 1-heptene, 1-octene, 1-decene or 4-methyl-1-pentene, or unsubstituted or substituted vinylaromatic compounds such as styrene and styrene derivatives, or dienes such as 1,3-butadiene, 1,4-hexadiene, 1,7-octadiene, 5-ethylidene-2-norbornene, norbornadiene, ethylnorbornadiene or cyclic olefins such as norbornene, tetracyclododecene or methylnorbornene.

The catalyst system of the invention is particularly preferably used for homopolymerizing ethylene or copolymerizing ethylene together with further α-olefins, in particular $C_3$-$C_8$-α-olefins such as propylene, 1-butene, 1-pentene, 1-hexene and/or 1-octene, and/or cyclic olefins such as norbornene and/or dienes having from 4 to 20 carbon atoms, e.g. 1,4-hexadiene, norbornadiene, ethylidenenorbornene or ethylnorbornadiene, particularly preferably for copolymerizing ethylene with propylene and/or 1-butene. Examples of such copolymers are ethylene/propylene, ethylene/1-butene, ethylene/1-hexene, ethylene/1-octene copolymers, ethylene/propylene/ethylidenenorbornene and ethylene/propylene/1,4-hexadiene terpolymers.

The polymerization can be carried out in a known manner in solution, in suspension, in the gas phase or in a supercritical medium in the customary reactors used for the polymerization of olefins. It can be carried out batchwise or preferably continuously in one or more stages. Solution processes, suspension processes, stirred gas-phase processes or gas-phase fluidized-bed processes are all possible. As solvents or suspension media, it is possible to use inert hydrocarbons, for example isobutane, or a suitable monomer or comonomer itself.

The polymerization can be carried out at temperatures in the range from –60° C. to 300° C. and pressures in the range from 0.5 to 3000 bar. Preference is given to temperatures in the range from 50° C. to 200° C., in particular from 60° C. to 150° C., very particularly preferably from 70° C. to 120° C., and pressures in the range from 5 to 100 bar, in particular from 15 to 70 bar. The mean residence times are usually from 0.5 to 5 hours, preferably from 0.5 to 3 hours. As molar mass regulator and/or to increase the activity, it is possible to use, for example, hydrogen, diethylzinc, carbon monoxide, carbon dioxide or oxygen in the polymerization. Furthermore, customary additives such as antistatics can also be employed. The catalyst system of the invention can be used directly in the polymerization, i.e. it is introduced in undiluted form into the polymerization system, or it is admixed with inert components such as paraffins, oils or waxes to improve meterability.

The novel organometallic transition metal compounds of the formula (I) or (II) and the catalyst systems in which they are present are especially useful for preparing ethylene homopolymers or copolymers based on ethylene, in each case having high molar masses and a defined chain structure.

The ethylene homopolymer or ethylene copolymer prepared using the novel organometallic transition metal compounds of the formula (I) or (II) or the catalyst systems in which they are present can also be constituent of a polymer blend. The type of further polymer components in the blend depends on the way in which the polymer blend is to be used later. Blending can be achieved, for example, by mixing with one or more additional LLDPEs or HDPEs or LDPEs. Alternatively, the polymer blend can also be achieved by simultaneous polymerization using one or more catalyst systems which are likewise active in the polymerization of olefins. As further catalysts for the preparation of blend polymers or for simultaneous polymerization, it is possible to use, in particular, classical Ziegler-Natta catalysts based on titanium, classical Phillips catalysts based on chromium oxides or single-site catalysts which preferably comprise, as transition metal component, metallocenes, viz. constrained geometry complexes (cf., for example, EPA 0 416 815 or EP A 0 420 436), chromium single-site complexes as are described, for example, in U.S. Pat. No. 6,437,161, nickel and palladium bisimine systems (which can be prepared as described in WO 9803559 A1) or iron and cobalt pyridinebisimine compounds (which can be prepared as described in WO 9827124 A1). However, the further catalyst system can also be based on another organometallic transition metal compound according to the invention having the formula (I) or (II). The further catalyst systems can likewise be supported.

The ethylene homopolymer or ethylene copolymer prepared using the novel organometallic transition metal compounds of the formula (I) or (II) or the catalyst systems in which they are present can also form bimodal mixtures with other olefin polymers, in particular ethylene homopolymers and ethylene copolymers. These can be obtained either by means of the above-described simultaneous presence of a further catalyst suitable for the polymerization of olefins or by subsequent blending of the separately prepared polymers or copolymers.

The blends which comprise the ethylene homopolymers or ethylene copolymers prepared using the novel organometallic transition metal compounds of the formula (I) or (II) or the catalyst systems in which they are present can also further comprise two or three other olefin polymers or copolymers. These can be, for example, LDPEs (blends thereof are described, for example, in DE-A1-19745047) or polyethylene homopolymers (blends thereof are described, for example, in EP-B-100843), LLDPEs (as described, for example, in EP-B-728160 or WO-A-90/03414) or LLDPE/LDPEs (WO 95/27005 or EP-B1-662989).

The ethylene copolymers, polymer mixtures and blends can further comprise known auxiliaries and/or additives such as processing stabilizers, stabilizers against the effects of light and heat, customary additives such as lubricants, antioxidants, antiblocking agents and antistatics, and also, if appropriate, colorants. A person skilled in the art will be familiar with the type and amount of these additives.

Furthermore, it has been found that additions of small amounts of fluororubbers or thermoplastic polyesters enable a further improvement in the processing properties of the ethylene homopolymers or ethylene copolymers prepared using the novel organometallic transition metal compounds of the formula (I) or (II) or the catalyst systems in which they are present to be achieved. Such fluororubbers are known as processing aids and are commercially available, e.g. under the trade names Viton and Dynamar (cf., for example, U.S. Pat. No. 3,125,547). They are preferably added in amounts of from 10 to 1000 ppm, particularly preferably from 20 to 200 ppm, based on the total mass of the ethylene homopolymers or ethylene copolymers prepared using the novel or ganometallic transition metal compounds of the formula (I) or (II) or the catalyst systems in which they are present.

The ethylene homopolymers or ethylene copolymers prepared using the novel organometallic transition metal compounds of the formula (I) or (II) or the catalyst systems in which they are present can also be modified subsequently by grafting, crosslinking, hydrogenation, functionalization or other functionalization reactions known to those skilled in the art.

The polymer blends can be produced by all known methods. This can be achieved, for example, by feeding the powder components to a pelletization apparatus, e.g. a twin-screw kneader (TSK) or Farrel kneader. It is also possible to process a mixture of pellets directly on a film production plant.

The polymer blends are, for example, very useful for producing films on blown film and cast film plants at high outputs. The films comprising the polymer blends display very good mechanical properties, high shock resistance and high tear strength combined with good optical properties. They are suitable, in particular, for the packaging sector, both for heavy-duty sacks and for the food sector. Furthermore, the films display only a slight blocking tendency and can therefore be handled on machines with only small additions, if any, of lubricants and antiblocking agents.

Owing to their good mechanical properties, the olefin copolymers prepared using the catalyst system of the invention are likewise suitable for producing fibers and moldings produced by injection molding or blow molding.

The invention is illustrated by the following nonlimiting examples.

EXAMPLES

General

Preparation and handling of the organometallic compounds and their use as catalyst component was carried out in the absence of air and moisture under argon (Schlenk technique or glove-box). All solvents required were purged with argon and dried over molecular sieves before use.

Example 1

Synthesis of 8-$\eta^5$-[2-(3-methylcyclopenta[b]benzothienylidene]-7-$\eta^5$-(9-fluorenylidene)-1-octenezirconium dichloride (1)

a) Preparation of 8-[2-(3-methylcyclopenta[b]benzothien-2-yl]-7-(9-fluorenyl)-1-octene (1a)

16 ml of an n-butyllithium solution (40 mmol, 16 ml, 2.5 M in hexane) were added dropwise to a solution of 6.64 g (40 mmol) of fluorene in 80 ml of diethyl ether at room temperature and the reaction mixture was stirred for another hour. A solution of 4.8 g (38 mmol) of 1,2-epoxy-7-octene in 20 ml of diethyl ether was then slowly added thereto. After the reaction mixture had been stirred for another hour, 7.6 g (40 mmol) of p-toluenesulfonyl chloride was slowly added as a solid. Separately from this first reaction mixture, a solution of a mixture of 7.4 g (40 mmol) of 2-methyl-3H-cyclopenta[b][1]benzothiophene/2-methyl-1H-cyclopenta[b][1]benzothiophene in 70 ml of diethyl ether was admixed with 16 ml of an n-butyllithium solution (40 mmol, 16 ml, 2.5 M in hexane) and the mixture was stirred for another hour. The second reaction mixture was added dropwise to the first reaction mixture comprising 2-(9H-fluoren-9-yl)oct-7-enyl p-toluenesulfonate, the resulting mixture was stirred for 18 hours and subsequently subjected to an aqueous work-up. After phase separation, the organic phase was washed with water, dried over magnesium sulfate and the solvent was removed under reduced pressure. This gave 17.6 g of a deep orange oil which was chromatographed on silica gel (dichloromethane/hexane 1:9). This gave 3.07 g of (1a) (yield 17.5%) as a viscous yellow oil.

MS: m/e 460 (M+).

b) Preparation of 8-$\eta^5$-[2-(3-methylcyclopenta[b]benzothienylidene]-7-$\eta^5$-(9-fluorenylidene)-1-octenezirconium dichloride (1)

5.2 ml of an n-butyllithium solution (13 mmol, 2.5 M in hexane) were added dropwise to a solution of 3.07 g (6.6 mmol) of 8-[2-(3-methylcyclopenta[b][1]benzothien-2-yl]-7-(9-fluorenyl)-1-octene in 70 ml of diethyl ether at room temperature and the reaction mixture was stirred for another 4 hours. 1.53 g (6.6 mmol) of zirconium tetrachloride were added slowly to this reaction mixture. After stirring for another 18 hours, the reaction mixture was filtered, the filtrate was concentrated and 0.98 g of precipitated solid were isolated. A second amount of solid was isolated and washed with pentane. A total of 2.08 g of (1) (yield 51%) were obtained as a bright orange free-flowing powder.

Example 2

Synthesis of 8-$\eta^5$-[6-(3-phenyl-2,5-dimethylcyclopenta[b]thienylidene)]-7-$\eta^5$-[4-indeno[b]thienylidene)]-1-octenezirconium dichloride (2)

a) 8-[6-(3-Phenyl-2,5-dimethylcyclopenta[b]thienyl)]-7-[4-indeno[b]thienyl)]-1-octene (2a)

Using a method analogous to the synthesis of compound (1a) in Example 1, 1.72 g (10 mmol) of 4H-indeno[b]thiophene in 50 ml of diethyl ether were reacted with n-butyllithium (10 mmol, 4 ml, 2.5 M in hexane) and, after 2 hours, 1.26 g (10 mmol) of 1,2-epoxy-7-octene (without solvent) were added. After a further 2 hours, 1.9 g (10 mmol) of p-toluenesulfonyl chloride were added. After 18 hours, a solution of 2,5-dimethyl-3-phenylthiopentalenelithium (2.26 g, 10 mmol dissolved in 80 ml of diethyl ether) was added dropwise. The reaction mixture was stirred for a further 18 hours and poured into water.

After phase separation, the organic phase was washed with water, dried over magnesium sulfate and the solvent was removed under reduced pressure. This gave 4.78 g of a deep orange oil which was chromatographed on silica gel (dichloromethane/hexane 1:9). This gave 3.0 g of (2a) (yield 59%) as a viscous yellow oil.

MS: m/e 506 (M+).

$^1$H-NMR (CDCl$_3$) δ ppm; 6.9-8.2 (m, 12H), 6.2-6.7 (3s, 1H), 5.7-5.9 (m, 1H), 5.0 (m, 2H), 4.2-4.6 (m, 1H), 4.0 (m, 1H), 2.6 (2s, 3H), 2.2 (m, 4H), 1.2-1.7 m, 4H).

b) Preparation of 8-$\eta^5$-[6-(3-phenyl-2,5-dimethylcyclopenta[b]thienylidene)]-7-$\eta^5$-[4-indeno[b]thienylidene)]-1-octenezirconium dichloride (2)

Using a method analogous to the synthesis of compound (1) in Example 1, 3.0 g of the compound (2a) in 70 ml of diethyl ether was reacted with n-butyllithium (12 mmol, 4.8 ml, 2.5 M in hexane) and, after 4 hours, admixed with 1.37 g (5.9 mmol) of zirconium tetrachloride. After stirring for another 18 hours, the reaction mixture was filtered, the filtrate was concentrated and 0.5 g of precipitated solid was isolated. A second amount of solid was isolated. A total of 1.0 g of (2) (yield 25.4%) was obtained as an orange free-flowing powder.

$^1$H-NMR (CDCl$_3$) δ ppm; 6.9-8.0 (m, 12H), 6.0 (2s, 1H), 5.8 (m, 1H), 5.0 (t, 2H), 4.3 (m, 1H), 3.9 (m, 2H), 2.5 (2s, 3H), 2.1, (2s, 6H), 1.2-1.6 (m, 4H).

Example 3

Synthesis of 8-$\eta^5$-[6-(2,5-dimethylcyclopenta[b]thienylidene)]-7-$\eta^5$-(9-fluorenylidene)-1-octenezirconium dichloride (3)

a) Preparation of 8-[6-(2,5-dimethylcyclopenta[b]thienyl)]-7-$\eta^5$-(9-fluorenyl)-1-octene (3a)

Using a method analogous to the synthesis of compound (1a) in Example 1, 4.5 g (30 mmol) of 2,5-dimethyl-4H-cyclopenta[b]thiophene in 80 ml of diethyl ether were reacted with n-butyllithium (30 mmol, 12 ml, 2.5 M in hexane). After 3 hours, a solution of 11.1 g (30 mmol) of 2-(9H-fluoren-9-yl)oct-7-enyl methanesulfonate prepared by a method analogous to that used for the corresponding p-toluenesulfonic ester in Example (1a) in 15 ml of diethyl ether was added. The reaction mixture was stirred for 48 hours and admixed with 2 ml of saturated ammonium chloride solution. The reaction mixture was poured into water. After phase separation, the aqueous phase was extracted with dichloromethane/hexane (30:70), the combined organic phases were washed with water, dried over magnesium sulfate and the solvent was removed under reduced pressure. This gave 11.64 g of a dark orange oil which was chromatographed on silica gel (330 g) (dichloromethane/hexane 15:85; 30 ml/min). This gave 5.0 g of (3a) as a viscous yellow oil.

b) Preparation of 8-$\eta^5$-[6-(2,5-dimethylcyclopenta[b]thienylidene)]-7-$\eta^5$-(9-fluorenylidene)-1-octenezirconium dichloride (3)

Using a method analogous to the synthesis of compound (1) in Example 1, 4.24 g of the compound (3a) in 100 ml of diethyl ether were reacted with n-butyllithium (20 mmol, 8 ml, 2.5 M in hexane) and, after 4 hours, admixed with 2.33 g (10 mmol) of zirconium tetrachloride. After stirring for another 18 hours, the reaction mixture was filtered, the residue on the filter was washed with fresh diethyl ether and the combined filtrates were completely freed of solvent under reduced pressure. 3.81 g of red powder were isolated. The residue which remained on the filter was extracted with dichloromethane and the filtrate was subsequently freed completely of solvent. A red powder was likewise isolated, and according to $^1$H-NMR this did not differ from the first powder obtained. The solid fractions were combined to give 4.43 g of a dark red free-flowing powder.

Example 4

Synthesis of 8-$\eta^5$-[6-(3-(o-tolyl)-2,5-dimethylcyclopenta[b]thienylidene)]-7-$\eta^5$-(9-fluorenylidene)-1-octenezirconium dichloride (4)

a) Preparation of 8-[6-(3-(o-tolyl)-2,5-dimethylcyclopenta[b]thienyl)]-7-$\eta^5$-(9-fluorenyl)-1-octene (4a)

Using a method analogous to the synthesis of compound (3a) in Example 3, 2.97 g (12.4 mmol) of 2,5-dimethyl-3-o-tolyl-4H-cyclopenta[b]thiophene prepared as described in J. Am. Chem. Soc. 2001, 123, 4763-4773) and dissolved in 80 ml of diethyl ether were reacted with n-butyllithium (12.5 mmol, 5 ml, 2.5 M in hexane). After 4 hours, a solution of 4.58 g (12.4 mmol) of 2-(9H-fluoren-9-yl)oct-7-enyl methanesulfonate in 10 ml of diethyl ether was added. The reaction mixture was stirred for 48 hours and admixed with 2 ml of saturated ammonium chloride solution. The reaction mixture was poured into water. After phase separation, the aqueous phase was extracted with dichloromethane/hexane (30:70), the combined organic phases were washed with water, dried over magnesium sulfate and the solvent was removed under reduced pressure. This gave 6.31 g of a dark brown oil which was chromatographed on silica gel (dichloromethane/hexane 20:80). This gave 1.6 g of (4a) as a viscous yellow oil.

b) Preparation of 8-$\eta^5$-[2-(5-(o-tolyl)-3,6-dimethyl-cyclopenta[d]thienylidene)]-7-$\eta^5$-(9-fluorenylidene)-1-octenezirconium dichloride (4)

Using a method analogous to the synthesis of compound (1) in Example 1, 1.6 g (3.1 mmol) of the compound (4a) in 60 ml of diethyl ether were reacted with n-butyllithium (6.2 mmol, 2.5 ml, 2.5 M in hexane) and, after 18 hours, admixed with 0.72 g (3.1 mmol) of zirconium tetrachloride. After stirring for another 4 hours, the reaction mixture was filtered, the residue on the filter was washed with fresh diethyl ether and the combined filtrates were freed completely of solvent under reduced pressure. 1.26 g of red powder were isolated. The residue which remained on the filter was extracted with dichloromethane and the filtrate was subsequently freed completely of solvent. A red powder was likewise isolated, and according to $^1$H-NMR this did not differ from the first powder obtained. The solid fractions were combined to give 1.25 g of a dark red free-flowing powder.

Example 5

Synthesis of 8-$\eta^5$-[6-(3-phenyl-2,5-dimethylcyclopenta[b]thienylidene)]-7-$\eta^5$-(9-fluorenylidene)-1-octenezirconium dichloride (5)

a) Preparation of 8-[6-(3-phenyl-2,5-dimethylcyclopenta[b]thienyl)]-7-$\eta^5$-(9-fluorenyl)-1-octene (5a)

Using a method analogous to the synthesis of compound (3a) in Example 3, 3.0 g (13.3 mmol) of 2,5-dimethyl-3-phenyl-4H-cyclopenta[b]thiophene prepared as described in J. Am. Chem. Soc. 2001, 123, 4763-4773, and dissolved in 80 ml of diethyl ether were reacted with n-butyllithium (13.3 mmol, 5.3 ml, 2.5 M in hexane). After 3 hours, a solution of 4.58 g (13.3 mmol) of 2-(9H-fluoren-9-yl)oct-7-enyl methanesulfonate in 15 ml of diethyl ether was added. The reaction mixture was stirred for 48 hours and admixed with 2 ml of saturated ammonium chloride solution. The reaction mixture was poured into water. After phase separation, the aqueous phase was extracted with dichloromethane/hexane (30:70), the combined organic phases were washed with water, dried over magnesium sulfate and the solvent was removed under reduced pressure. This gave 6.65 g of a dark brown oil which was chromatographed on silica gel (dichloromethane/hexane 20:80). This gave 1.57 g of (5a) as a viscous yellow oil.

b) Preparation of 8-$\eta^5$-[6-(3-phenyl-2,5-dimethylcyclopenta[b]thienylidene)]-7-$\eta^5$-(9-fluorenylidene)-1-octenezirconium dichloride (5)

Using a method analogous to the synthesis of compound (1) in Example 1, 1.57 g (3.1 mmol) of the compound (5a) in 80 ml of diethyl ether were reacted with n-butyllithium (6.2 mmol, 2.5 ml, 2.5 M in hexane) and, after 18 hours, admixed with 0.72 g (3.1 mmol) of zirconium tetrachloride. After stirring for another 18 hours, the reaction mixture was filtered, the residue on the filter was washed with fresh diethyl ether and the combined filtrates were freed completely of solvent under reduced pressure. The solid residue was washed with pentane and dried. 0.93 g of red powder was isolated. The residue remaining on the filter was extracted with dichloromethane and the filtrate was subsequently freed completely of solvent. A red powder was likewise isolated. The solid fractions were combined to give a total of 2.62 g of (5) in the form of a dark red powder.

Polymerization Examples and Polymerization Results

General:
Heptane was dried over 3 Å molecular sieves. Water-free pentane (Aldrich) was used without further purification. Methylaluminoxane was used as a 30% strength solution in toluene (Albemarle Corporation).

Polymer Analysis:
The intrinsic viscosity ($\eta$)[dl/g] was determined at 135° C. on an automatic Ubbelohde viscometer (Lauda PVS 1) using decalin as solvent (ISO1628 at 135° C., 0.001 g/ml of decalin).

The density [g/cm$^3$] of the polymer samples was determined in accordance with ISO1183.

The molar mass distributions and the means $M_n$, $M_w$ and $M_w/M_n$, derived therefrom were determined by means of high-temperature gel permeation chromatography using a method based on DIN 55672 on a WATERS 150 C with the following columns connected in series: 3× SHODEX AT 806 MS, 1× SHODEX UT 807 and 1× SHODEX AT-G under the following conditions: solvent: 1,2,4-trichlorobenzene (stabilized with 0.025% by weight of 2,6-di-tert-butyl-4-methylphenol), flow: 1 ml/min, 500 µl injection volume, temperature: 135° C., calibration using PE standards. Evaluation was carried out by means of WIN-GPC.

Van Gurp-Palmen plots were prepared on the basis of rheological measurements on the polymer samples carried out on a shear-stress-controlled rotational rheometer from "Rheometric Scientific" (name: Dynamic Stress Rheometer SR 2000; geometry: PP25 h=1 mm; shear stress: 1000 Pa). Evaluation of the rheological measurements was carried out as described in the following two references:

Stefan Trinkle, Christian Friedrich: Van Gurp-Palmen-plot: a way to characterize polydispersity of linear polymers, Rheol. Acta (2001) 40, 322-328

Stefan Trinkle, Philipp Walter, Christian Friedrich: Van Gurp-Palmen-plot II: classification of long chain branched polymers by their topology, Rheol. Acta (2002) 41, 103-113

General Preparation of the Catalyst Solutions 10 mg of metallocene were dissolved in 100 ml of toluene. 1 ml of this metallocene solution in toluene was added to the calculated amount of methylaluminoxane solution, with a color change being observed. The catalyst solution was stirred for 10 minutes before use.

General Method for the Homogeneous Polymerization of Ethylene

The polymerizations were carried out in a 1 l steel autoclave provided with a mechanical stirrer and a jacket thermostated by means of oil for temperature control. The autoclave was flushed with dry nitrogen for one hour at 90° C. prior to the polymerization. After cooling to 30° C., 500 ml of heptane as solvent and a defined amount of aluminum alkyl to react with impurities were introduced into the reactor. A catalyst solution prepared by the above method was introduced into the reactor by means of a syringe. The stirrer was set to 300 revolutions per minute and the internal temperature of the reactor was increased to 80° C. Ethylene was fed into the reactor until the total internal pressure in the reactor was 10 bar. The internal pressure in the reactor was maintained at 10 bar for 30 minutes by introduction of ethylene. The stirrer was then switched off, the introduction of ethylene was stopped, the reactor was depressurized and cooled to room temperature. The reactor was flushed with nitrogen and 5 ml of methanol were introduced into the reactor before it was opened. The contents of the reactor were filtered and the polymer which had been filtered off was dried at 50° C. under reduced pressure for 4 hours before weighing.

stirring until the weight was constant. 183 g of the catalyst system were obtained.

Example B 0.44 g of the complex from Example 3 were dissolved in 15.7 ml of a 30% strength MAO solution in toluene and the mixture was stirred for 1 hour. The supernatant solution was decanted off and added dropwise over a period of 15 minutes to 12 g of silica (Ineos silicas ES70X, calcined at 600° C. for 6 hours) with moderate stirring. After stirring for a further 60 minutes, volatile constituents were removed at room temperature under reduced pressure with occasional stirring over a period of 4 hours until the weight was constant. 17 g of the catalyst system were obtained.

Example C 4.9 g of the complex from Example 1 were dissolved in 206 ml of a 30% strength MAO solution in toluene and the mixture was stirred for 3.5 hours. The supernatant solution was decanted off and added dropwise over a period of 15 minutes to 158 g of silica (Ineos silicas ES70X, calcined at 600° C. for 6 hours) with moderate stirring. After stirring for a further 30 minutes, volatile constituents were removed at room temperature under reduced pressure with occasional stirring until the weight was constant. 288 g of the catalyst system were obtained. The residual moisture content was 34.8%, the Al content was 5.8 g/100 g and the Zr content was 0.12 g/100 g.

TABLE 1

Results of the polymerization of ethylene using unsupported catalyst systems

| Example | Complex from Example | $Al_{MAO}/TM$ [mol/mol] | Activity [kg/g * h] | IV | Melting point [° C.] | Heater fusion [J/g] | TiBAl [mmol] |
|---------|---------|------|------|-----|-----|-----|---|
| P1 | 1 | 5898 | 1000 | 3.7 | 147 | 196 | 4 |
| P2 | 3 | 5555 | 400 | 3.5 | 145 | 196 | 4 |
| P3 | 2 | 4752 | 460 | 2.6 | 145 | 183 | 4 |
| P4 | 4 | 5005 | 392 | 2.8 | 141 | 202 | 4 |
| P5 | 5 | 5012 | 568 | 3.0 | 145 | 193 | 2 |

Polymerization conditions: 500 ml of heptane, 10 bar of ethylene, 30 minutes' polymerization time;
Units and abbreviations: $Al_{MAO}/TM$ is the molar ratio of aluminum from the MAO to the transition metal complex; activity in $kg_{polymer}/(g_{transition\ metal\ compound} * h_{polymerization\ time})$;
IV is the intrinsic viscosity [η] determined in decalin at 135° C.;
melting points and heats of fusion were determined by means of DSC.

Preparation of the Supported Catalyst Systems

Example A 2.18 g of the complex from Example 1 were dissolved in 92 ml of a 30% strength MAO solution in toluene and the mixture was stirred for 1 hour. The supernatant solution was decanted off and added dropwise over a period of 15 minutes to 140.5 g of silica (Grace Davison XPO 2107, calcined at 600° C. for 6 hours) with moderate stirring. After stirring for a further 20 minutes, volatile constituents were removed at room temperature under reduced pressure with occasional General Method for the Polymerization of Ethylene in Suspension The polymerizations were carried out in a stirred 10 l steel autoclave which had a thermostatted jacket for temperature control. After careful flushing with nitrogen and heating to the polymerization temperature of 70° C., 5 l of isobutane and 100 mg of isoprenylaluminum were placed in the autoclave. The supported catalyst system was then added as a solid and the autoclave was pressurized with ethylene to a total pressure of 40 bar. The pressure in the autoclave was kept constant by introduction of further ethylene. After 90 minutes, the polymerization was stopped by venting the autoclave. The polymer was obtained in the form of a free-flowing coarse powder.

TABLE 2

Polymerization results

| Example | Catalyst from Example | Weight used [mg] | Productivity [g/g] | IV | Density | $M_w$/1000 | $M_w/M_n$ |
|---|---|---|---|---|---|---|---|
| P6 | A | 403 | 2060 | 6.0 | 0.9413 | 723 | 7.3 |
| P7 | B | 437 | 1396 | 7.7 | 0.9416 | 821 | 7.1 |

Polymerization conditions: 5000 ml of isobutane, 40 bar of ethylene, 90 minutes' polymerization time;
Units and abbreviations: productivity in $g_{polymer}/g_{catalyst\ system}$;
IV is the intrinsic viscosity [η] determined in decalin at 135° C.;
$M_w$ is the weight average molar mass;
$M_w/M_n$ (weight average/number average molar mass) characterizes the width of the molar mass distribution;
$M_w$ and $M_n$ were determined by means of GPC General Method for the Copolymerization of Ethylene and 1-Hexene in Suspension The polymerizations were carried out in a stirred 10 l steel autoclave which had a thermostatted jacket for temperature control. After careful flushing with nitrogen and heating to the polymerization temperature of 70° C., 4.7 l of isobutane, 300 ml of 1-hexene and 100 mg of isoprenylaluminum were placed in the autoclave. The supported catalyst system was then added as a solid and the autoclave was pressurized with ethylene to a total pressure of 40 bar. The pressure in the autoclave was kept constant by introduction of further ethylene. After 90 minutes, the polymerization was stopped by venting the autoclave. The polymer was obtained in the form of a free-flowing coarse powder.

TABLE 3

Polymerization results

| Example | Catalyst from Example | Weight used [mg] | Productivity [g/g] | IV | Density | $M_w$/1000 | $M_w/M_n$ |
|---|---|---|---|---|---|---|---|
| P8 | A | 414 | 3092 | 3.5 | 0.9256 | 441 | 6.3 |
| P9 | B | 458 | 1834 | 4.0 | 0.9402 | 368 | 6.0 |

Polymerization conditions: 4700 ml of isobutane, 300 ml of 1-hexene, 40 bar of ethylene, 90 minutes' polymerization time;
Units and abbreviations: productivity in $g_{polymer}/g_{catalyst\ system}$;
IV is the intrinsic viscosity [η] determined in decalin at 135° C.;
$M_w$ is the weight average molar mass;
$M_w/M_n$ (weight average/number average molar mass) characterizes the width of the molar mass distribution;
$M_w$ and $M_n$ were determined by means of GPC General Method for the Copolymerization of Ethylene and 1-Hexene in the Gas Phase in an Autoclave The polymerizations were carried out in a 1 l steel autoclave provided with a mechanical stirrer and a thermostatted jacket for temperature control. The autoclave was made inert by means of nitrogen and charged with 150 g of polyethylene powder at 70° C. 14.5 ml of heptane, 125 mg of isoprenylaluminum (50 mg per ml) in heptane and 10 mg of Costelan AS100 (5 mg per ml) in heptane were subsequently added and the mixture was stirred for 5 minutes. The supported catalyst system was added as a solid, the catalyst container was rinsed with 2 ml of heptane, the reactor was closed and stirred for 10 minutes. It was then pressurized firstly with 10 bar of argon and then with ethylene to a total pressure of 20 bar. 20% by volume of gaseous 1-hexene were introduced into the ethylene. The internal pressure in the reactor was maintained for 1 hour by introduction of further ethylene and 1-hexene. The stirrer was subsequently switched off, the introduction of ethylene was stopped, the reactor was depressurized and cooled to room temperature. The polymer is taken from the reactor and dried under reduced pressure.

TABLE 4

Polymerization results

| Example | Catalyst from Example | Weight used [mg] | Productivity [g/g] | IV | Density | $M_w$/1000 | $M_w/M_n$ |
|---|---|---|---|---|---|---|---|
| P10 | A | 54 | 870 | 2.7 | 0.9116 | 275 | 5.3 |
| P11 | B | 63 | 730 | 2.8 | 0.9182 | 265 | 6.2 |

Polymerization conditions: 10 bar of ethylene, 20% by volume of 1-hexene, 60 minutes' polymerization time;
Units and abbreviations: productivity in $g_{polymer}/g_{catalyst\ system}$;
IV is the intrinsic viscosity [η] determined in decalin at 135° C.;
$M_w$ is the weight average molar mass;
$M_w/M_n$ (weight average/number average molar mass) characterizes the width of the molar mass distribution;
$M_w$ and $M_n$ were determined by means of GPC General Method for Continuous Gas-Phase Polymerization In a continuously operated gas-phase fluidized-bed reactor, ethylene-hexene copolymers were prepared at a reactor pressure of 20 bar and a reactor temperature of 85° C. using the supported catalyst system from Example C. 6 kg/h of ethylene and also 1-hexene and hydrogen were fed into the reactor for reaction. In addition, 0.58 kg/h of nitrogen, hexane, 0.1 g/h of triisobutylaluminum and 0.033 g/h of Costelan AS100 as a solution in heptane were fed in. The supported catalyst system was introduced into the reactor as a solid in an amount of 1.38 g/h.

TABLE 5

Polymerization results

| Example | Catalyst from Ex. | Polymer designation | Hexene feed [g/h] | Hydrogen feed [l/h] | Hexane addition [g/h] | Productivity [g/g] | IV | Density [g/cm³] | $M_w$/1000 | $M_w/M_n$ |
|---|---|---|---|---|---|---|---|---|---|---|
| P12 | C | 703972 | 605 | 10.8 | 320 | 3998 | 1.35 | 0.921 | 86 | 7.1 |
| P13 | C | 703975 | 620 | 11.1 | 412 | 4203 | 1.4 | 0.9185 | 82 | 6.6 |

Figure 2:
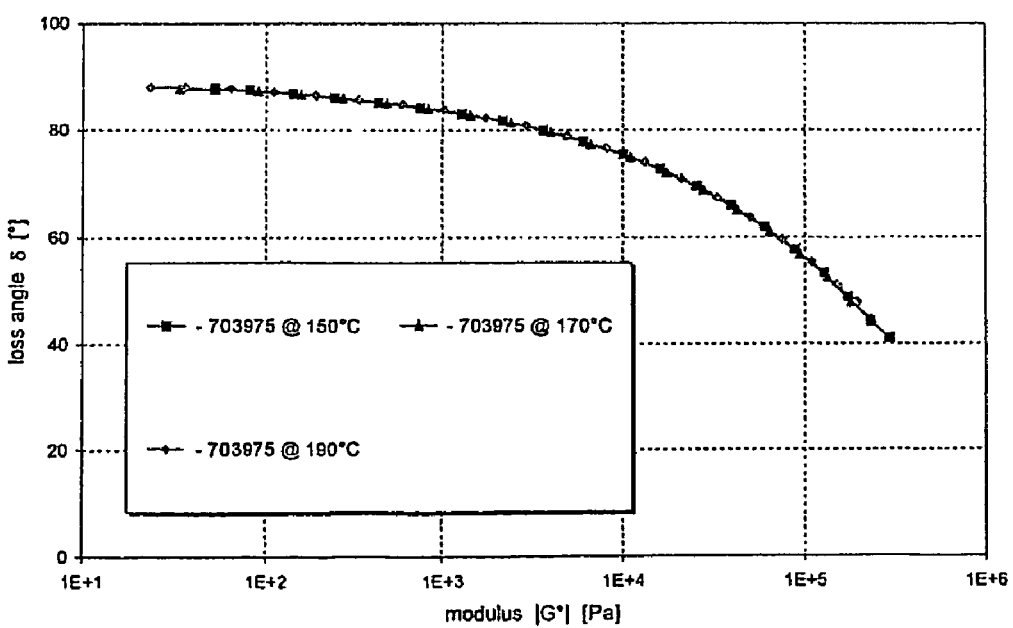
FIG. 2 illustrates a Van Gurp-Palmen plot for the polymer 703975.

Units and abbreviations: productivity in $g_{polymer}/g_{catalyst\ system}$;
IV is the intrinsic viscosity [η] determined in decalin at 135° C.;
$M_w$ is the weight average molar mass;
$M_w/M_n$ (weight average/number average molar mass) characterizes the width of the molar mass distribution;
$M_w$ and $M_n$ were determined by means of SEC The Van Gurp-Palmen plot for the polymer 703972 is shown in FIG. 1 and the Van Gurp-Palmen plot for the polymer 703975 is shown in FIG. 2.

The invention claimed is:

1. An organometallic transition metal compound according to formula (II)

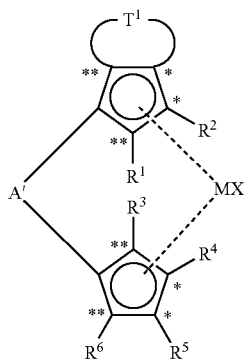

(II)

where
M is an element of group 4 of the Periodic Table of the Elements,
the radicals
X are identical or different and are each an organic or inorganic radical, with two radicals X also being able to be joined to one another,

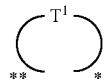

is a divalent group

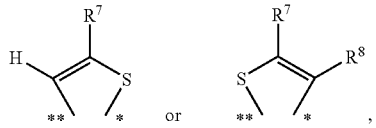

$R^1$ is an organic radical having from 1 to 40 carbon atoms,
$R^2$ is hydrogen,

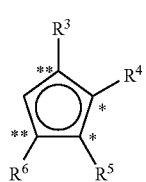

is a molecule fragment:

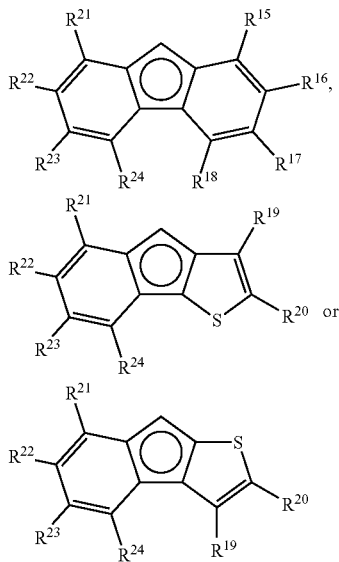

$R^7$ is an organic radical having from 1 to 40 carbon atoms, $R^8$ is hydrogen or an organic radical having from 1 to 40 carbon atoms or $R^7$ and $R^8$ together with the atoms connecting them form a monocyclic or polycyclic ring system which may in turn be substituted, $R^{15}$, $R^{16}$, $R^{17}$ and $R^{18}$ are identical or different and are each hydrogen or an organic radical having from 1 to 40 carbon atoms or two adjacent radicals $R^{15}$, $R^{16}$, $R^{17}$ or $R^{18}$ together with the atoms connecting them form a monocyclic or polycyclic ring system which may in turn be substituted, $R^{19}$, $R^{20}$ are identical or different and are each hydrogen or an organic radical having from 1 to 40 carbon atoms or $R^{19}$ and $R^{20}$ together with the atoms connecting them form a monocyclic or polycyclic ring system which may in turn be substituted, $R^{21}$, $R^{22}$, $R^{23}$ and $R^{24}$ are identical or different and are each hydrogen or an organic radical having from 1 to 40 carbon atoms or two adjacent radicals $R^{21}$, $R^{22}$, $R^{23}$ or $R^{24}$ together with the atoms connecting them form a monocyclic or polycyclic ring system which may in turn be substituted, A' is

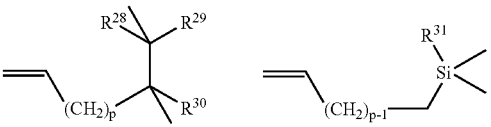

where $R^{28}$, $R^{29}$, $R^{30}$ and $R^{31}$ are identical or different and are each hydrogen or an organic radical having from 1 to 40 carbon atoms or two radicals $R^{28}$, $R^{29}$ and $R^{30}$ together with the atoms connecting them form a monocyclic or polycyclic ring system which may in turn be substituted, p is from 2 to 8.

2. A catalyst system for the polymerization of olefins which comprises at least one organometallic transition metal compound according to claim 1 and at least one cocatalyst which is able to convert the organometallic transition metal compound into a species which displays polymerization activity toward at least one olefin.

3. The catalyst system according to claim 2 which further comprises a support.

4. A process for preparing an organometallic transition metal compound, which comprises reacting a ligand system of the formula (IV):

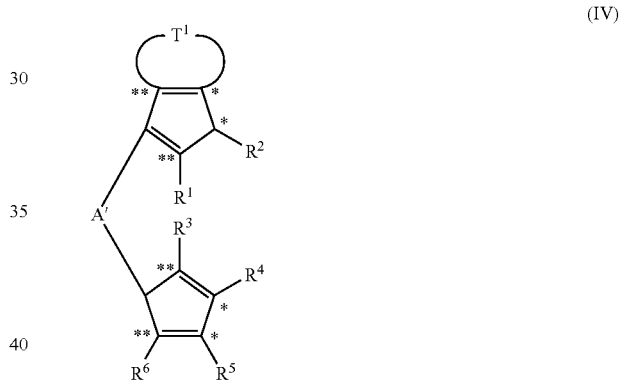

(IV)

or its double bond isomers, wherein the variables are as defined in formula (II) of claim 1, or a bisanion prepared therefrom, with a transition metal compound.

\* \* \* \* \*